(12) United States Patent
Ando et al.

(10) Patent No.: US 7,141,608 B2
(45) Date of Patent: *Nov. 28, 2006

(54) CALCIUM DICARBOXYLATE ETHERS, METHODS OF MAKING SAME, AND TREATMENT OF VASCULAR DISEASE AND DIABETES THEREWITH

(75) Inventors: Howard Yoshihisa Ando, Ypsilanti, MI (US); Donald Eugene Butler, Holland, MI (US); Gary Jay Dozeman, Zeeland, MI (US)

(73) Assignee: Warmer-Lambert Company LLC, Morris Plains, NJ (US)

( * ) Notice: Subject to any disclaimer, the term of this patent is extended or adjusted under 35 U.S.C. 154(b) by 53 days.

This patent is subject to a terminal disclaimer.

(21) Appl. No.: 10/938,203

(22) Filed: Sep. 10, 2004

(65) Prior Publication Data

US 2005/0032902 A1   Feb. 10, 2005

Related U.S. Application Data

(63) Continuation of application No. 10/018,617, filed as application No. PCT/IB01/00026 on Jan. 11, 2001, now Pat. No. 6,861,555.

(60) Provisional application No. 60/177,823, filed on Jan. 25, 2000.

(51) Int. Cl.
   *A01N 37/00*   (2006.01)

(52) U.S. Cl. .................................... 514/574; 562/568
(58) Field of Classification Search .................... None
   See application file for complete search history.

(56) References Cited

U.S. PATENT DOCUMENTS

| 5,648,387 A | 7/1997 | Bisgaier et al. |
| 5,756,544 A * | 5/1998 | Bisgaier et al. ............. 514/547 |
| 6,861,555 B1 * | 3/2005 | Ando et al. ................. 562/568 |

FOREIGN PATENT DOCUMENTS

| WO | WO-96/30328 | 10/1996 |
| WO | WO-99/30704 | 6/1999 |

* cited by examiner

*Primary Examiner*—Paul A. Zucker
(74) *Attorney, Agent, or Firm*—Charles W. Ashbrook; William R. Boudreaux; Claude F. Purchase

(57) ABSTRACT

Alcohol and water solvates of 6-(5-carboxy-5-methyl-hexyloxy)-2,2-dimethylhexanoic acid monocalcium salt are crystalline and have the formula

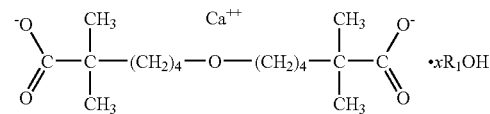

wherein $R_1$ is H or lower alkyl, and x is a number from 0 to 10, and are useful for treating dyslipidemia.

9 Claims, 27 Drawing Sheets

| # | 2-Theta | d(A) | Peak | P% | Area | Area% | FWHM |
|---|---------|---------|------|-------|------|-------|-------|
| 1 | 6.760 | 13.0648 | 5106 | 100.0 | 1497 | 100.0 | 0.234 |
| 2 | 8.183 | 10.7953 | 1743 | 34.1 | 435 | 29.1 | 0.200 |
| 3 | 8.560 | 10.3207 | 1866 | 36.5 | 543 | 36.3 | 0.233 |
| 4 | 9.239 | 9.5638 | 234 | 4.6 | 29 | 1.9 | 0.096 |
| 5 | 9.760 | 9.0546 | 972 | 19.0 | 220 | 14.7 | 0.181 |
| 6 | 10.569 | 8.3634 | 156 | 3.1 | 12 | 0.8 | 0.061 |
| 7 | 11.141 | 7.9353 | 178 | 3.5 | 29 | 1.9 | 0.130 |
| 8 | 13.760 | 6.4304 | 266 | 5.2 | 46 | 3.1 | 0.138 |
| 9 | 15.599 | 5.6761 | 338 | 6.6 | 63 | 4.2 | 0.148 |
| 10 | 16.740 | 5.2917 | 433 | 8.5 | 64 | 4.3 | 0.118 |
| 11 | 17.420 | 5.0866 | 1890 | 37.0 | 689 | 46.0 | 0.291 |
| 12 | 20.639 | 4.3000 | 523 | 10.2 | 128 | 8.5 | 0.196 |
| 13 | 21.391 | 4.1505 | 188 | 3.7 | 20 | 1.3 | 0.085 |
| 14 | 22.139 | 4.0119 | 445 | 8.7 | 74 | 4.9 | 0.132 |
| 15 | 31.559 | 2.8326 | 270 | 5.3 | 24 | 1.6 | 0.070 |

FIG. 1A

| # | 2-Theta | d(A) | Peak | P% | Area | Area% | FWHM |
|---|---------|---------|-------|-------|------|-------|-------|
| 1 | 6.899 | 12.8028 | 13186 | 100.0 | 3025 | 100.0 | 0.184 |
| 2 | 8.261 | 10.6945 | 5221 | 39.6 | 931 | 30.8 | 0.143 |
| 3 | 8.838 | 9.9969 | 2057 | 15.6 | 482 | 15.9 | 0.187 |
| 4 | 11.061 | 7.9927 | 785 | 6.0 | 160 | 5.3 | 0.163 |
| 5 | 12.100 | 7.3086 | 1355 | 10.3 | 150 | 4.9 | 0.088 |
| 6 | 13.619 | 6.4964 | 450 | 3.4 | 89 | 2.9 | 0.157 |
| 7 | 17.677 | 5.0132 | 753 | 5.7 | 126 | 4.2 | 0.134 |
| 8 | 18.180 | 4.8755 | 2011 | 15.3 | 588 | 19.4 | 0.234 |
| 9 | 20.840 | 4.2588 | 439 | 3.3 | 40 | 1.3 | 0.072 |
| 10 | 21.334 | 4.1615 | 427 | 3.2 | 67 | 2.2 | 0.125 |

FIG. 2A

| # | 2-Theta | d(A) | Peak | P% | Area | Area% | FWHM |
|---|---------|---------|------|-------|------|-------|-------|
| 1 | 6.959 | 12.6918 | 8224 | 100.0 | 2809 | 100.0 | 0.273 |
| 2 | 8.381 | 10.5414 | 2375 | 28.9 | 732 | 26.0 | 0.246 |
| 3 | 8.701 | 10.1544 | 2107 | 25.6 | 742 | 26.4 | 0.282 |
| 4 | 9.383 | 9.4176 | 328 | 4.0 | 25 | 0.9 | 0.060 |
| 5 | 9.941 | 8.8906 | 1160 | 14.1 | 356 | 12.7 | 0.245 |
| 6 | 13.975 | 6.3317 | 330 | 4.0 | 26 | 0.9 | 0.062 |
| 7 | 15.778 | 5.6120 | 244 | 3.0 | 38 | 1.3 | 0.121 |
| 8 | 16.920 | 5.2357 | 597 | 7.3 | 213 | 7.6 | 0.284 |
| 9 | 17.540 | 5.0521 | 2206 | 26.8 | 729 | 25.9 | 0.264 |
| 10 | 20.799 | 4.2672 | 407 | 4.9 | 71 | 2.5 | 0.138 |
| 11 | 22.261 | 3.9902 | 563 | 6.8 | 107 | 3.8 | 0.152 |

FIG. 3A

| # | 2-Theta | d(A) | Peak | P% | Area | Area% | FWHM |
|---|---------|---------|-------|-------|------|-------|-------|
| 1 | 6.896 | 12.8072 | 11991 | 100.0 | 2593 | 100.0 | 0.173 |
| 2 | 8.339 | 10.5940 | 2046 | 17.1 | 334 | 12.9 | 0.131 |
| 3 | 9.219 | 9.5853 | 1438 | 12.0 | 281 | 10.8 | 0.156 |
| 4 | 10.280 | 8.5979 | 632 | 5.3 | 180 | 6.9 | 0.227 |
| 5 | 11.320 | 7.8105 | 1079 | 9.0 | 322 | 12.4 | 0.238 |
| 6 | 15.800 | 5.6044 | 463 | 3.9 | 59 | 2.3 | 0.102 |
| 7 | 16.741 | 5.2913 | 432 | 3.6 | 38 | 1.4 | 0.069 |
| 8 | 18.160 | 4.8809 | 1260 | 10.5 | 599 | 23.1 | 0.380 |
| 9 | 18.702 | 4.7408 | 700 | 5.8 | 184 | 7.1 | 0.210 |
| 10 | 19.816 | 4.4766 | 589 | 4.9 | 94 | 3.6 | 0.127 |
| 11 | 21.724 | 4.0876 | 510 | 4.3 | 96 | 3.7 | 0.150 |

FIG. 4A

| # | 2-Theta | d(A) | Peak | P% | Area | Area% | FWHM |
|---|---------|---------|-------|-------|------|-------|-------|
| 1 | 6.901 | 12.7988 | 10206 | 100.0 | 2683 | 100.0 | 0.210 |
| 2 | 8.360 | 10.5679 | 2545 | 24.9 | 524 | 19.5 | 0.164 |
| 3 | 8.680 | 10.1792 | 1459 | 14.3 | 359 | 13.4 | 0.197 |
| 4 | 9.279 | 9.5230 | 580 | 5.7 | 91 | 3.4 | 0.125 |
| 5 | 9.879 | 8.9456 | 794 | 7.8 | 143 | 5.3 | 0.143 |
| 6 | 11.321 | 7.8094 | 577 | 5.7 | 97 | 3.6 | 0.133 |
| 7 | 15.780 | 5.6113 | 523 | 5.1 | 95 | 3.5 | 0.144 |
| 8 | 17.541 | 5.0519 | 1710 | 16.8 | 418 | 15.6 | 0.195 |
| 9 | 18.702 | 4.7408 | 459 | 4.5 | 116 | 4.3 | 0.201 |
| 10 | 19.877 | 4.4631 | 403 | 3.9 | 67 | 2.5 | 0.133 |

FIG.5A

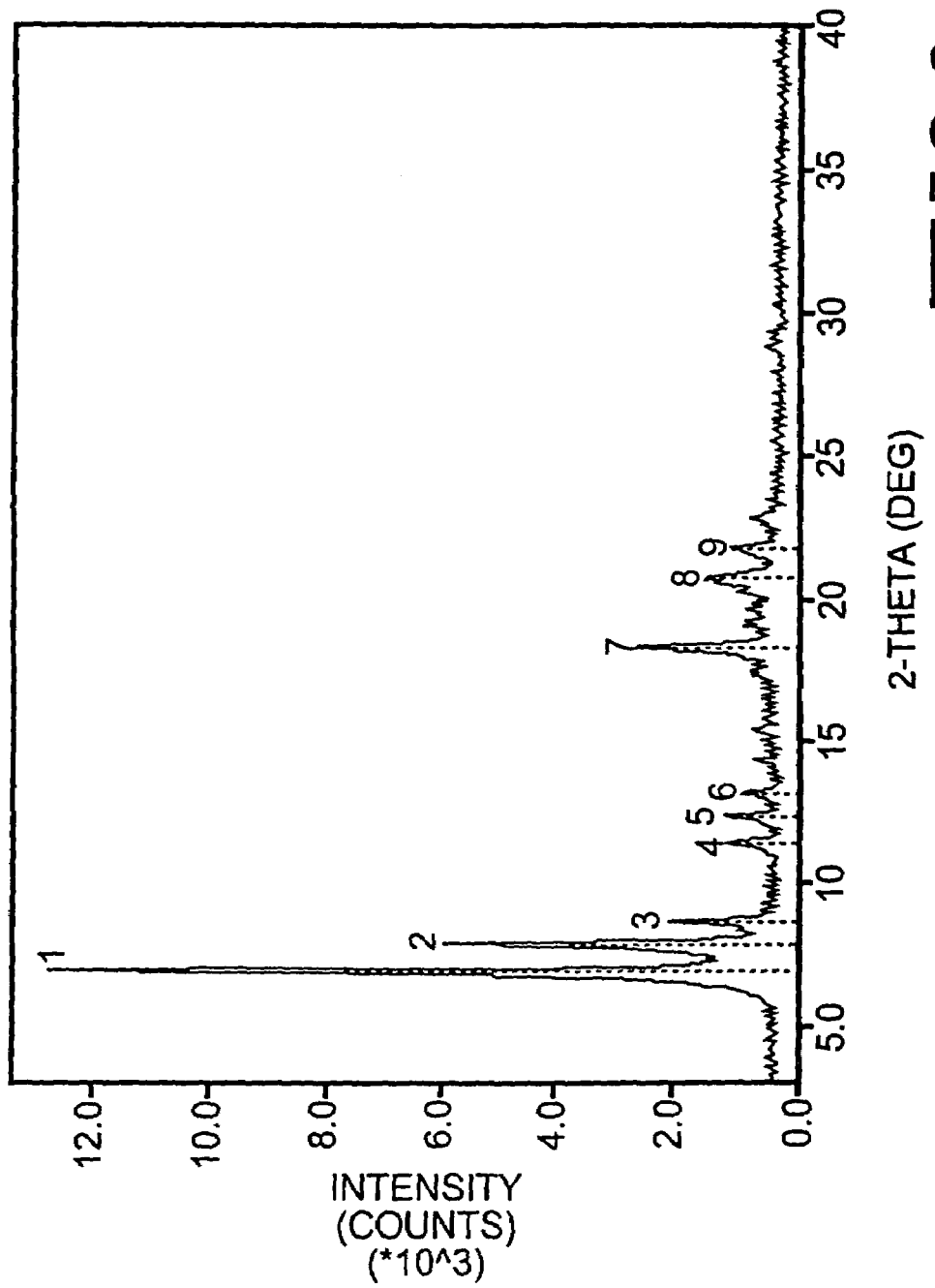

| # | 2-Theta | d(A) | Peak | P% | Area | Area% | FWHM |
|---|---------|---------|-------|-------|------|-------|-------|
| 1 | 6.899 | 12.8025 | 12371 | 100.0 | 3495 | 100.0 | 0.226 |
| 2 | 7.843 | 11.2637 | 4815 | 38.9 | 1119 | 32.0 | 0.186 |
| 3 | 8.661 | 10.2009 | 1709 | 13.8 | 357 | 10.2 | 0.167 |
| 4 | 11.359 | 7.7833 | 771 | 6.2 | 141 | 4.0 | 0.146 |
| 5 | 12.300 | 7.1900 | 752 | 6.1 | 127 | 3.6 | 0.135 |
| 6 | 13.100 | 6.7528 | 517 | 4.2 | 37 | 1.0 | 0.057 |
| 7 | 18.262 | 4.8540 | 1945 | 15.7 | 596 | 17.1 | 0.245 |
| 8 | 20.721 | 4.2832 | 828 | 6.7 | 279 | 8.0 | 0.269 |
| 9 | 21.740 | 4.0847 | 573 | 4.6 | 146 | 4.2 | 0.203 |

FIG.6A

| # | 2-Theta | d(A) | Peak | P% | Area | Area% | FWHM |
|---|---------|---------|------|-------|------|-------|-------|
| 1 | 6.939 | 12.7278 | 9980 | 100.0 | 2717 | 100.0 | 0.218 |
| 2 | 8.381 | 10.5414 | 2850 | 28.6 | 790 | 29.1 | 0.222 |
| 3 | 8.640 | 10.2253 | 2267 | 22.7 | 772 | 28.4 | 0.272 |
| 4 | 9.419 | 9.3815 | 487 | 4.9 | 32 | 1.2 | 0.051 |
| 5 | 9.840 | 8.9812 | 1288 | 12.9 | 255 | 9.4 | 0.158 |
| 6 | 13.940 | 6.3476 | 374 | 3.7 | 56 | 2.0 | 0.118 |
| 7 | 15.741 | 5.6253 | 450 | 4.5 | 45 | 1.6 | 0.079 |
| 8 | 16.861 | 5.2539 | 580 | 5.8 | 192 | 7.0 | 0.264 |
|   | 17.560 | 5.0464 | 2604 | 26.1 | 846 | 31.1 | 0.260 |
| 10 | 20.743 | 4.2787 | 508 | 5.1 | 73 | 2.7 | 0.114 |
| 11 | 22.321 | 3.9796 | 542 | 5.4 | 156 | 5.7 | 0.229 |

FIG. 7A

| # | 2-Theta | d(A) | Peak | P% | Area | Area% | FWHM |
|---|---------|---------|-------|-------|------|-------|-------|
| 1 | 6.918 | 12.7674 | 10028 | 100.0 | 2562 | 100.0 | 0.204 |
| 2 | 8.000 | 11.0427 | 3984 | 39.7 | 800 | 31.2 | 0.161 |
| 3 | 8.619 | 10.2506 | 1619 | 16.1 | 346 | 13.5 | 0.171 |
| 4 | 11.338 | 7.7981 | 658 | 6.6 | 68 | 2.6 | 0.082 |
| 5 | 11.718 | 7.5459 | 236 | 2.4 | 28 | 1.1 | 0.093 |
| 6 | 12.241 | 7.2243 | 761 | 7.6 | 131 | 5.1 | 0.138 |
| 7 | 15.382 | 5.7557 | 610 | 6.1 | 107 | 4.2 | 0.140 |
| 8 | 18.162 | 4.8803 | 1937 | 19.3 | 441 | 17.2 | 0.182 |
| 9 | 20.779 | 4.2713 | 853 | 8.5 | 222 | 8.6 | 0.208 |

FIG.8A

| # | 2-Theta | d(A) | Peak | P% | Area | Area% | FWHM |
|---|---------|---------|------|-------|------|-------|-------|
| 1 | 6.877 | 12.8422 | 8063 | 100.0 | 2195 | 100.0 | 0.218 |
| 2 | 8.330 | 10.6062 | 2501 | 31.0 | 800 | 36.4 | 0.256 |
| 3 | 8.581 | 10.2965 | 1898 | 23.5 | 514 | 23.4 | 0.217 |
| 4 | 9.356 | 9.4446 | 432 | 5.4 | 45 | 2.0 | 0.082 |
| 5 | 9.799 | 9.0191 | 1064 | 13.2 | 275 | 12.5 | 0.207 |
| 6 | 13.864 | 6.3821 | 293 | 3.6 | 58 | 2.6 | 0.158 |
| 7 | 15.721 | 5.6322 | 312 | 3.9 | 67 | 3.0 | 0.170 |
| 8 | 17.480 | 5.0693 | 2458 | 30.5 | 898 | 40.9 | 0.292 |
| 9 | 20.818 | 4.2633 | 299 | 3.7 | 67 | 3.0 | 0.178 |
| 10 | 22.280 | 3.9869 | 416 | 5.2 | 106 | 4.8 | 0.202 |

FIG. 9A

| # | 2-Theta | d(A) | Peak | P% | Area | Area% | FWHM |
|---|---------|--------|-------|-------|------|-------|-------|
| 1 | 7.060 | 12.5101 | 19609 | 100.0 | 4796 | 100.0 | 0.196 |
| 2 | 9.078 | 9.7332 | 3027 | 15.4 | 567 | 11.8 | 0.150 |
| 3 | 11.100 | 7.9644 | 924 | 4.7 | 164 | 3.4 | 0.142 |
| 4 | 16.361 | 5.4135 | 554 | 2.8 | 76 | 1.6 | 0.109 |
| 5 | 18.040 | 4.9133 | 2276 | 11.6 | 456 | 9.5 | 0.160 |
| 6 | 18.820 | 4.7112 | 1303 | 6.6 | 385 | 8.0 | 0.236 |
| 7 | 19.922 | 4.4532 | 1886 | 9.6 | 457 | 9.5 | 0.193 |
| 8 | 21.560 | 4.1183 | 853 | 4.4 | 205 | 4.3 | 0.191 |
| 9 | 22.281 | 3.9867 | 343 | 1.7 | 37 | 0.8 | 0.086 |
| 10 | 23.521 | 3.7793 | 450 | 2.3 | 107 | 2.2 | 0.189 |

FIG. 10A

| # | 2-Theta | d(A) | Peak | P% | Area | Area% | FWHM |
|---|---------|---------|------|-------|------|-------|-------|
| 1 | 7.018 | 12.5854 | 9344 | 100.0 | 2618 | 100.0 | 0.224 |
| 2 | 8.432 | 10.4775 | 2599 | 27.8 | 676 | 25.8 | 0.208 |
| 3 | 8.722 | 10.1302 | 2091 | 22.4 | 697 | 26.6 | 0.266 |
| 4 | 9.499 | 9.3030 | 378 | 4.0 | 33 | 1.2 | 0.069 |
| 5 | 9.980 | 8.8560 | 1243 | 13.3 | 337 | 12.9 | 0.217 |
| 6 | 14.000 | 6.3206 | 390 | 4.2 | 64 | 2.4 | 0.130 |
| 7 | 15.861 | 5.5830 | 550 | 5.9 | 46 | 1.7 | 0.066 |
| 8 | 16.881 | 5.2479 | 595 | 6.4 | 115 | 4.4 | 0.154 |
| 9 | 17.622 | 5.0287 | 3006 | 32.2 | 1053 | 40.2 | 0.280 |
| 10 | 20.918 | 4.2431 | 718 | 7.7 | 113 | 4.3 | 0.126 |
| 11 | 21.641 | 4.1031 | 318 | 3.4 | 44 | 1.7 | 0.110 |
| 12 | 22.380 | 3.9693 | 573 | 6.1 | 144 | 5.5 | 0.201 |

FIG. 11A

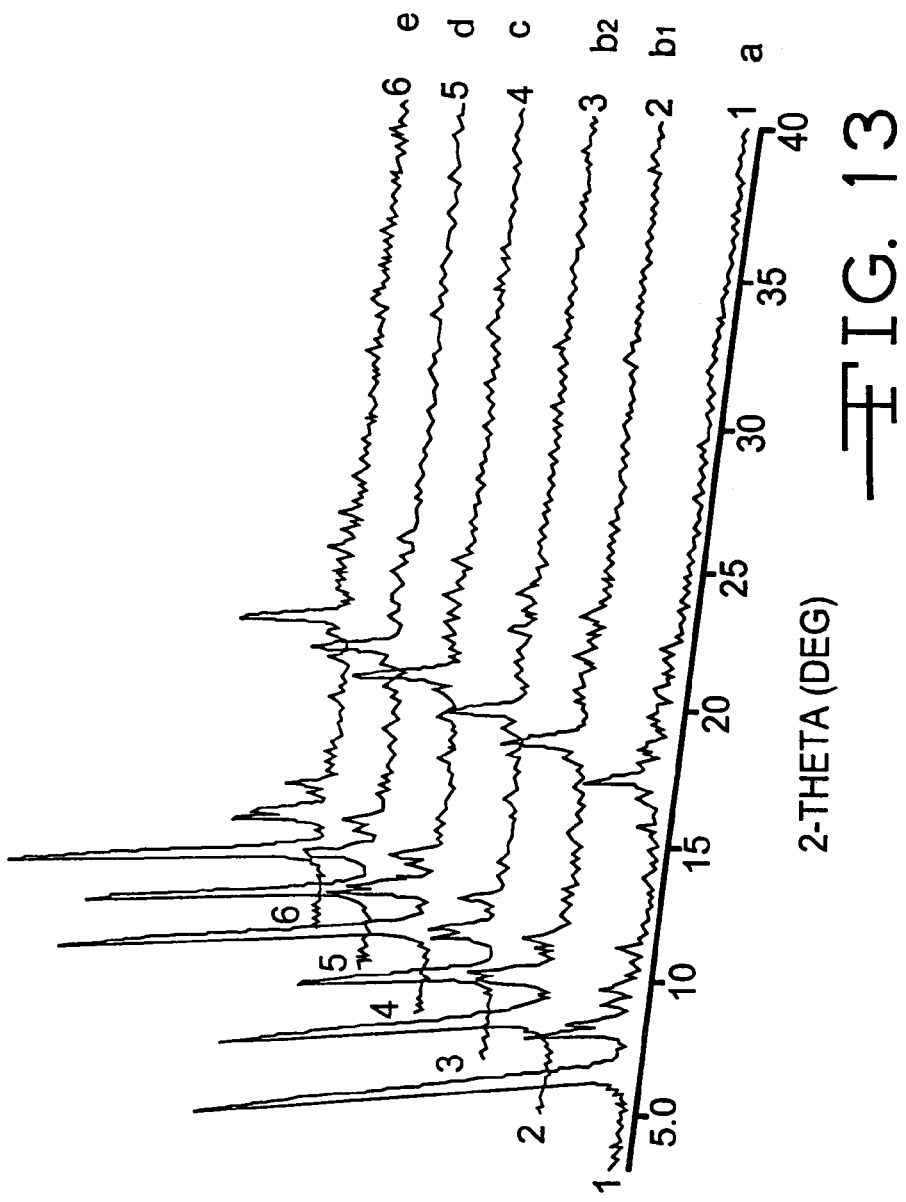

FIG. 13 a - SOLVENT FREE CRYSTALLINE FORM FROM METHYL ALCOHOL SOLVATE
b1 - SOLVENT FREE CRYSTALLINE FORM FROM ETHYL ALCOHOL SOLVATE (LAB SCALE)
b2 - SOLVENT FREE CRYSTALLINE FORM FROM ETHYL ALCOHOL SOLVATE (PILOT SCALE)
c - SOLVENT FREE CRYSTALLINE FORM FROM 1-PROPYL ALCOHOL SOLVATE
d - SOLVENT FREE CRYSTALLINE FORM FROM 2-PROPYL ALCOHOL SOLVATE
e - SOLVENT FREE CRYSTALLINE FORM FROM 1-BUTYL ALCOHOL SOLVATE

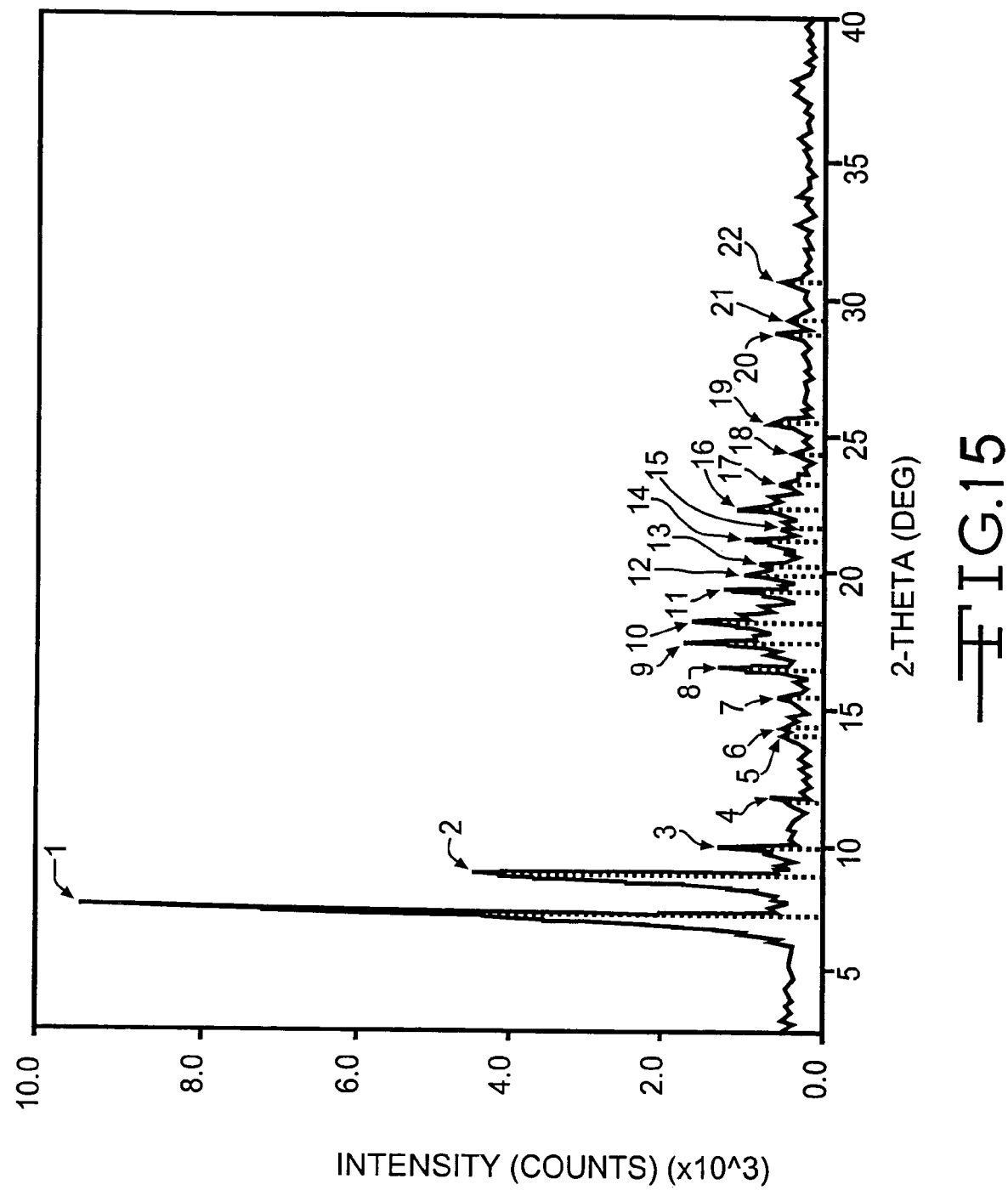

| #  | 2-THETA | d(A)    | PEAK | P%   | AREA | AREA% | FWHM  |
|----|---------|---------|------|------|------|-------|-------|
| 1  | 7.259   | 12.1686 | 9283 | 100  | 2482 | 100   | 0.214 |
| 2  | 8.739   | 10.1100 | 4191 | 45.1 | 603  | 24.3  | 0.115 |
| 3  | 9.386   | 8.9628  | 967  | 10.4 | 161  | 6.5   | 0.133 |
| 4  | 11.659  | 7.5838  | 430  | 4.6  | 49   | 1.9   | 0.089 |
| 5  | 13.955  | 6.3408  | 305  | 3.3  | 58   | 2.3   | 0.151 |
| 6  | 14.220  | 6.2233  | 326  | 3.5  | 73   | 2.9   | 0.178 |
| 7  | 15.387  | 5.7537  | 278  | 3.0  | 19   | 0.7   | 0.053 |
| 8  | 16.461  | 5.3806  | 986  | 10.6 | 187  | 7.5   | 0.152 |
| 9  | 17.361  | 5.1039  | 1490 | 16.1 | 348  | 14.0  | 0.187 |
| 10 | 18.063  | 4.9069  | 1284 | 13.8 | 323  | 13.0  | 0.201 |
| 11 | 19.302  | 4.5947  | 871  | 9.4  | 166  | 6.7   | 0.152 |
| 12 | 19.862  | 4.4664  | 686  | 7.4  | 142  | 5.7   | 0.166 |
| 13 | 20.200  | 4.3923  | 457  | 4.9  | 103  | 4.1   | 0.179 |
| 14 | 21.178  | 4.1918  | 656  | 7.1  | 97   | 3.9   | 0.117 |
| 15 | 21.641  | 4.1031  | 167  | 1.8  | 6    | 0.2   | 0.029 |
| 16 | 22.300  | 3.9833  | 794  | 8.6  | 192  | 7.7   | 0.193 |
| 17 | 23.218  | 3.8278  | 247  | 2.7  | 23   | 0.9   | 0.071 |
| 18 | 24.100  | 3.6897  | 183  | 2.0  | 34   | 1.3   | 0.145 |
| 19 | 25.481  | 3.4928  | 487  | 5.2  | 141  | 5.7   | 0.231 |
| 20 | 28.800  | 3.0974  | 134  | 1.4  | 14   | 0.6   | 0.083 |
| 21 | 29.297  | 3.0459  | 259  | 2.8  | 28   | 1.1   | 0.084 |
| 22 | 30.700  | 2.9099  | 287  | 3.1  | 20   | 0.8   | 0.055 |

FIG.15A

CALCIUM DICARBOXYLATE ETHERS, METHODS OF MAKING SAME, AND TREATMENT OF VASCULAR DISEASE AND DIABETES THEREWITH

This application is a §120 continuation of U.S. patent application Ser. No. 10/018,617 filed Dec. 17, 2001, now U.S. Pat. No. 6,861,555 B2, which is a §371 of PCT/IB01/00026 filed Jan. 11, 2001, which claims benefit of U.S. Provisional Patent Application No. 60/177,823 filed Jan. 25, 2000.

FIELD OF THE INVENTION

The present invention relates to 6-(5-carboxy-5-methyl-hexyloxy)-2,2-dimethylhexanoic acid monocalcium salt (1:1), 6-(5-carboxy-5-methyl-hexyloxy)-2,2-dimethylhexanoic acid monocalcium salt (1:1) solvates, methods of producing 6-(5-carboxy-5-methyl-hexyloxy)-2,2-dimethylhexanoic acid monocalcium salt (1:1) in crystalline forms, methods of producing 6-(5-carboxy-5-methyl-hexyloxy)-2,2-dimethylhexanoic acid monocalcium salt (1:1) alcohol solvates in crystalline forms, and the treatment of disease therewith. In particular, the 6-(5-carboxy-5-methyl-hexyloxy)-2,2-dimethylhexanoic acid monocalcium salt (1:1) and solvates thereof of the present invention are useful for lowering certain plasma lipids in animals including Lp(a), triglycerides, VLDL-cholesterol, and LDL-cholesterol, as well as elevating HDL cholesterol. The compounds are also useful for treating diabetes mellitus.

BACKGROUND OF THE INVENTION

Vascular diseases such as coronary heart disease, stroke, restenosis, and peripheral vascular disease, remain the leading cause of death and disability throughout the world. About 1.5 million people die each year in the United States alone from myocardial infarction resulting from congestive heart failure. While diet and life style can accelerate the onset of vascular diseases, genetic predisposition leading to dyslipidemia is a significant factor in vascular-related disabilities and deaths. "Dyslipidemia" means abnormal levels of lipoproteins in blood plasma.

Several risk factors have been associated with increased risk of vascular disease. Among these are the dyslipidemias of high levels of low-density lipoprotein (LDL) and low levels of high-density lipoproteins (HDL). The ratio of HDL-cholesterol to LDL-cholesterol is often used to assess the risk of vascular disease. A high ratio of HDL/LDL cholesterol is desirable. Compounds that increase this ratio by either lowering LDL or increasing HDL, or both, therefore are beneficial.

Studies also have shown that elevated levels of a modified form of LDL designated as lipoprotein(a), "Lp(a)," are detrimental. Elevated levels of Lp(a) have been associated with the development of atherosclerosis, coronary heart disease, myocardial infarction, stroke, cerebral infarction, and restenosis following balloon angioplasty. In fact, Lp(a) appears to be an excellent predictor of stroke potential. Accordingly, high concentrations of cholesterol in the form of Lp(a) are one of the major factors leading to death from heart disease. Compounds that lower Lp(a) are therefore beneficial.

U.S. Pat. No. 5,648,387 discloses 6-(5-carboxy-5-methyl-hexyloxy)-2,2-dimethylhexanoic acid and its effectiveness in lowering plasma concentrations of Lp(a), and in increasing HDL. The formation of pharmaceutically acceptable salts from the carboxylic acid is also described, for example, by reaction with bases including sodium hydroxide, potassium hydroxide, calcium hydroxide, sodium carbonate, triethylamine, pyridine, and ammonia. Owing to the low melting character of the carboxylic acid and the lack of crystallinity and hygroscopic nature of the contemplated salts thereof, drying and crystallization of large quantities such as mass production lots remains inconsistent. Thus, there exists a need for a salt of the carboxyalkyl ether which is effective in raising HDL, lowering plasma Lp(a), which is crystalline so it can be manufactured and processed on a commercial scale, and which is amenable to pharmaceutical formulation for the treatment of vascular disease. This invention provides a salt form that satisfies these needs.

SUMMARY OF THE INVENTION

This invention provides new chemical compounds, which are calcium dicarboxylate ethers. The invention more particularly provides compounds characterized as solvated or unsolvated forms of the monocalcium salt of 6-(5-carboxy-5-methyl-hexyloxy)-2,2-dimethylhexanoic acid. The calcium salt of this invention is also known as "CI-1027". The invention compounds have Formula II:

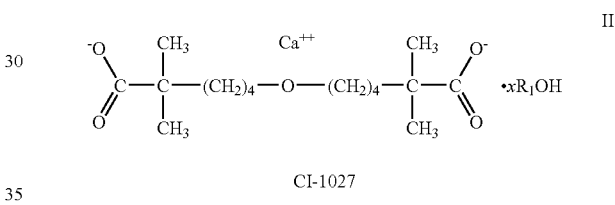

CI-1027 wherein:
$R_1$ is H or lower alkyl such as methyl, ethyl, 1-propyl, 2-propyl, and 1-butyl, and x is a number from 0 to 10. Preferred compounds are those wherein $R_1$ is H.

A preferred compound is CI-1027 Crystal Form 1 wherein $R_1$ is H and x is equivalent to about 3% to about 6% water content and having XRD of FIG. 1.

Another preferred compound is CI-1027 Crystal Form 2 wherein $R_1$ is H and x is equivalent to about 3% to about 6% water content and having XRD of FIG. 15.

Also preferred are nonsolvated forms of the salt, i.e., wherein x is zero.

A method of drying the calcium salt from organic alcohols is also provided. A method of crystallizing the monocalcium salt is a further embodiment.

A method of synthesizing the monocalcium dicarboxylate ether salts of Formula II is provided. The method includes exposing the dialkanoic ether acid to calcium oxide as the base in an organic alcoholic solvent. After allowing sufficient time for the reaction to occur, a solid product is removed and dried to yield a calcium dicarboxylate ether salt having a stoichiometric ratio of calcium to dicarboxylate ether of 1:1, solvated with an alcohol $R_1OH$. The alcohol $R_1OH$ solvate can be removed by drying with humidification of the drying chamber in vacuo. The calcium dicarboxylate ether salt having a stoichiometric ratio of calcium to dicarboxylate ether of 1:1 can be crystallized as a monohydrate by steam crystallization, namely by heating with water/water vapor at between 50° C. to 150° C. under pressure with agitation followed by vacuum drying. A second crystalline hydrate form can be obtained by heating the first form in water for an extended period of time, or alternatively by reacting the free acid of Formula I directly with calcium hydroxide and water at an elevated temperature of about 80° C. and recovering the solid by normal filtration.

The compounds of the present invention are useful as active ingredients in combination with pharmaceutically acceptable diluents, carriers, and excipients to treat vascular disease. The use of the calcium dicarboxylate ether salt, or a hydrate or alcohol solvate thereof, for the manufacture of a composition for the treatment of dyslipidemia, such as vascular disease, is also described within. The use of the calcium dicarboxylate ether salt and hydrate or alcohol solvate for the preparation of a composition for the treatment of diabetes is also described within.

BRIEF DESCRIPTION OF THE DRAWINGS

Other advantages of the present invention will be readily appreciated as the same become better understood by reference to the following detailed description when considered in connection with the accompanying drawings. In the drawings, the term "d(A)" means the d-spacing in angstroms. "P %" means the percentage of individual peaks relative to the most intense peak, which is equal to 100%. "Area" means area under the curve or peak. "FWHM" means the full width at half maximum measurement.

FIG. 1A are the numerical values given to the peaks shown in FIG. 1. (Each of the figures labeled A are the numerical values of the XRD trace to which the figure refers; e.g., 2A, 3A, etc.).

FIG. 6 is a two-dimensional drawing of the x-ray powder diffractogram of the 1-propyl alcohol solvate of CI-1027.

FIG. 13 is a three-dimensional comparison of x-ray powder diffractograms of the CI-1027 hydrate Crystal Form 1 derived from the solvates (a)–(e) depicted in FIG. 12.

FIG. 15 is a two-dimensional drawing of the x-ray diffractogram of CI-1027 hydrate (Crystal Form 2) after heating CI-1027 hydrate Crystal Form 1 with water and isolation and drying.

DETAILED DESCRIPTION OF THE INVENTION

Figure 1:
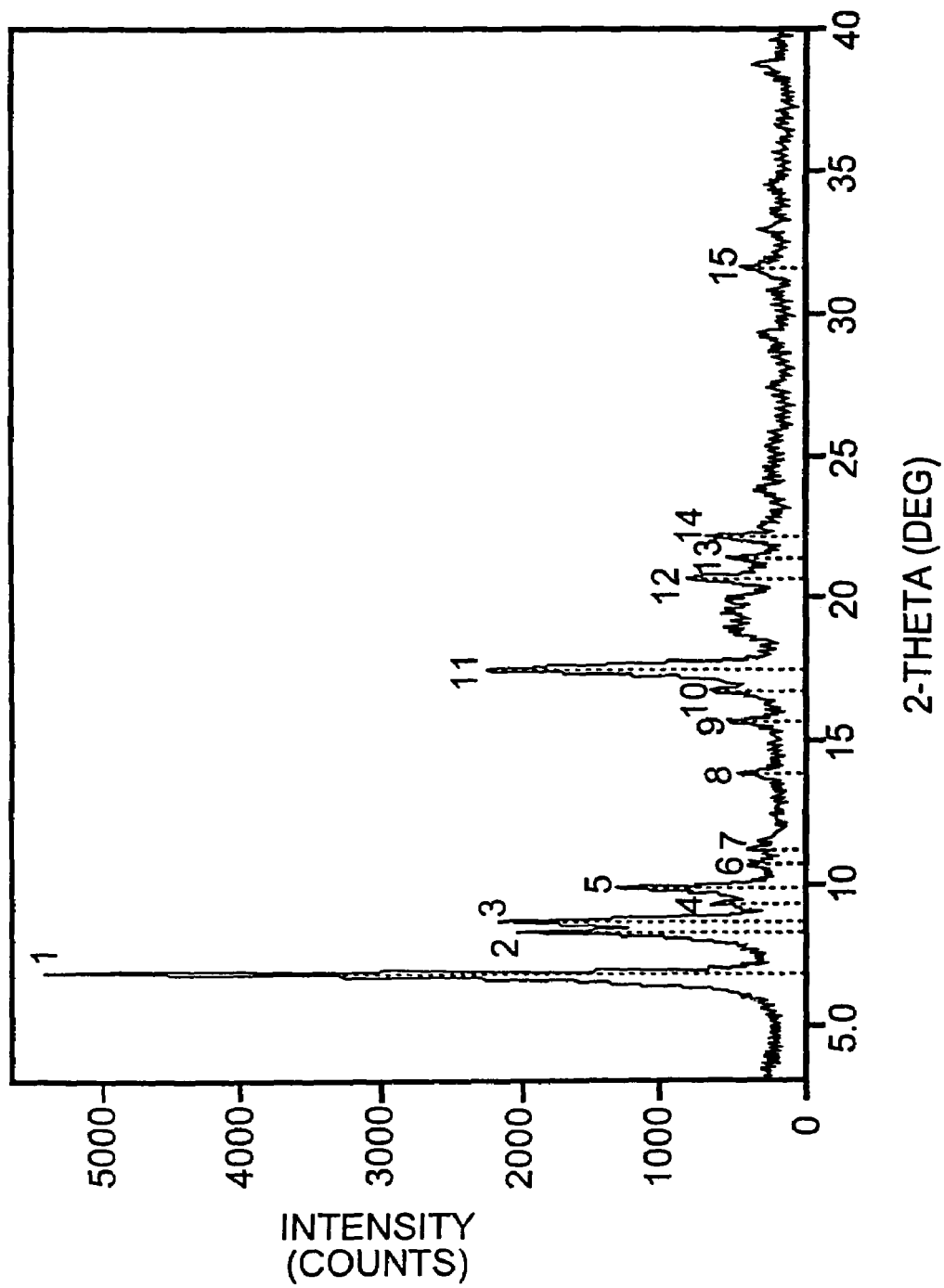
FIG. 1 is a two-dimensional drawing of the x-ray powder diffractogram of dicarboxylate ether monocalcium salt CI-1027 hydrate Crystal Form 1.

The compounds provided by this invention are prepared from a dialkylcarboxylic acid ether precursor. The synthesis of the precursor dialkylcarboxylic acid ether is described in U.S. Pat. No. 5,648,387, which is incorporated herein by reference. The precursor dialkylcarboxylic acid ether has the Formula I:

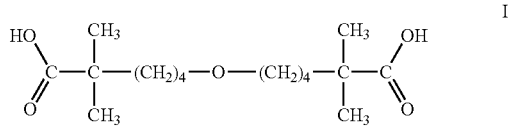

The diacid of Formula I is identified as 6-(5-carboxy-5-methyl-hexyloxy)-2,2-dimethylhexanoic acid. It is also known as "72953".

The calcium salts of Formula II that are provided by this invention are prepared by reacting the precursor dialkylcarboxylic acid ether (I) 72953 with a calcium base such as calcium oxide or calcium hydroxide. Calcium oxide is preferred. A small percentage of water can be present in the calcium oxide (up to about 5%). The reaction is preferably carried out in a solvent which dissolves the dialkylcarboxylic acid ether (I) and is at least only minimally reactive towards the calcium base. Preferably, the base such as calcium oxide partially dissolves in the solvent as well. Solvents operative in the present invention are alkanols, illustratively including $C_1$–$C_{12}$ alcohols, for example, methyl alcohol, ethyl alcohol, 1-propyl alcohol, 2-propyl alcohol, butanols, pentanols, cyclopentanol, hexanols, cyclohexanol, and the like. Preferably, the solvent is a $C_1$–$C_6$ absolute alcohol, and more preferably a $C_1$–$C_4$ alcohol.

The reaction of dialkylcarboxylic acid ether (I) with calcium oxide readily occurs at ambient or higher pressure, and a temperature of generally greater than about 25° C. is preferred. However, it is appreciated that the reaction is facilitated by heating the reaction mixture to the reflux point of the solvent, or even higher under pressure. Agitation further promotes uniform reaction throughout the reaction mixture. In order to assure conversion of most of the dialkylcarboxylic acid ether (I) to the mono-calcium salt, the molar ratio of calcium oxide to dialkylcarboxylic acid ether (I) should be between approximately 0.95 to approximately 1.05 molar equivalents. After allowing sufficient time for the reaction to occur between the dialkylcarboxylic acid ether (I) and the calcium oxide, a solid product is formed and recovered. Typically, the reaction is complete, in refluxing solvent, in from about 4 to about 96 hours. A compound of the present invention results having the following formula:

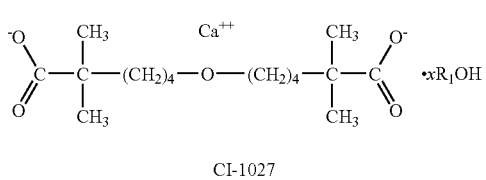

CI-1027 wherein $R_1$ is H or lower alkyl inclusive of methyl, ethyl, 1-propyl, 2-propyl, 1-butyl, and x is a number from 0 to about 10. In a preferred embodiment, $R_1$ is H (i.e., hydrates). Typically, the amount of water present in preferred salt forms ranges from about 3% to about 6% (e.g., x=0.03–0.06).

Optionally, following the reaction between the dialkylcarboxylic acid ether (I) and the calcium oxide, the reaction can be diluted by addition of a second solvent. The second solvent (also referred to as the work-up solvent) is preferably miscible with the reaction solvent such that any calcium salt dissolved in the reaction solvent tends to precipitate from the solvent mixture, and any unreacted organic materials remain in solution. It is appreciated that cooling the original solvent system or the mixed solvent system containing dialkylcarboxylic acid ether monocalcium salt (II) further induces precipitation. The identity of the added solvent is dictated, in part, by the identity of the reaction solvent. For example, in the case of the alcohols, methyl tert-butyl ether is a representative work-up (or second) solvent. Other work-up solvents can include diethyl ether, tetrahydrofuran, and $C_5$–$C_{12}$ mixed alkanes. However, any work-up solvent can be used, provided it is one in which the dialkylcarboxylic acid ether monocalcium salt (II) is substantially insoluble, and which can be readily removed by drying using normal conditions. Upon isolating the CI-1027 calcium salt, for instance by filtering or centrifuging off the solid product, the salt (II) is optionally washed with fresh work-up solvent, and is thereafter dried to remove the majority of the remaining water and solvent mixture. Drying is facilitated by heating the salt (II) to a temperature greater than room temperature and less than the decomposition temperature of the salt (II). Drying can be with hot air, heated inert gas, or in vacuo. Preferably, the CI-1027 salt (II) is heated to a temperature range from between about 60° C. and about 100° C. The product is substantially dry of solvents after about 1 to 3 hours. More preferably, the salt is heated under vacuum to further facilitate removal of the volatile solvents.

Surprisingly, it was discovered that heating and agitating the amorphous form of dialkylcarboxylic acid ether monocalcium salt (II) in the presence of water not only removed volatile solvents, but also caused the dialkylcarboxylic acid ether monocalcium salt (II) to become highly crystalline.

Humidification of the calcium salt (II) in a vacuum tray dryer facilitated the further removal of all volatile solvents to yield a crystalline form of dialkylcarboxylic acid ether calcium salt (II). The humidification can occur before or after complete drying of the dialkylcarboxylic acid ether monocalcium salt (II). Preferably, the solid monocalcium salt (II) is exposed to a humidification process prior to complete drying in order to facilitate removal of the volatile solvents to below the desired limit (e.g., below about 5%) and to promote crystallinity.

Thus, following partial drying of the salt in a heated vacuum chamber, water and water vapor is introduced to the partially dried dialkylcarboxylic acid ether monocalcium salt (II). Both drying operations are preferably done with agitation. After the humidification, vacuum is reapplied until the salt (II) attains a stable weight. The dialkylcarboxylic acid ether monocalcium salt (II) obtained following a humidification process is highly crystalline and has a bulk density following tapping of between about 0.3 g/mL and about 0.52 g/mL, with an average of about 0.4 g/mL. In contrast, the amorphous form of CI-1027 calcium salt (II) has a bulk density of about 0.2 g/mL to about 0.4 g/mL, with an average of about 0.3 gm/mL.

In a preferred embodiment, the invention provides two distinct polymorphs, namely CI-1027 Crystal Form 1 and CI-1027 Crystal Form 2. Heating a suspension of Crystalline Form 1 of the monocalcium salt in water to about 60° C. to 90° C. for extended periods of time, of about 6 to about 48 hours, converts it to the second crystalline form, designated Crystalline Form 2. The Crystalline Form 2 product can be prepared directly, if desired, by reacting the dialkylcarboxylic acid ether (I) with calcium hydroxide in water. These forms are distinguishable from one another by their respective x-ray powder diffraction patterns, as evidenced in FIGS. 1 and 15.

Crystal Forms 1 and 2 are preferred embodiments because they are observably less capable of retaining an electrostatic charge than salts of Formula II that are dried without exposure to humidification. The superior crystallinity of dialkylcarboxylic acid ether monocalcium salt (Forms 1 and 2), following the humidification process and a final drying, is indicated by the x-ray diffraction (XRD) analysis. X-ray powder diffractograms of solvated salts (II) are shown in the figures and indicate solvate formation within the solid product from methyl alcohol, ethyl alcohol, 1-propyl alcohol, 2-propyl alcohol, and 1-butanol. Additional analysis on the post-humidification dried dialkylcarboxylic acid ether monocalcium salt (II) is indicative of the formation of a salt which is associated with between about 0.1 and about 1 molar equivalent of water per equivalent of dialkylcarboxylic acid ether calcium salt (II), as shown in FIGS. 1 and 15, for example.

It is well-established in the art that unique crystal and polymorphic forms of compounds can be characterized by one or more unique 2-theta values in the x-ray diffractogram. While the Figures recite several 2-theta values, a single 2-theta value will suffice to identify a unique structure. Such unique structure forms also are identified by characteristic resonance peaks in the NMR, for instance, in the $^{13}C$ NMR spectrum.

The invention compounds of Formula II are useful pharmacological agents. The compounds have been shown to raise HDL and to lower triglycerides, LDL, and VLDL (see U.S. Pat. No. 5,783,600). They also lower Lp(a) (U.S. Pat. No. 5,750,569), and they can be used to treat noninsulin dependent diabetes mellitus (U.S. Pat. No. 5,756,544).

CI-1027 is currently being evaluated for clinical use in treating vascular diseases. Thus, the crystalline forms of this invention are of particular importance since they will facilitate commercial manufacture and use of a life-saving medication. A further embodiment of this invention is a method of treating vascular disease and diabetes comprising administrating to a mammal in need of treatment an effective amount of a compound of Formula II. An "effective amount" is the dose required to treat or prevent the vascular disease or diabetes of the mammal. The compounds are typically administered at a dose of about 50 to about 5000 mg/day, more generally about 50 to 2000 mg/day. A commonly employed dosage is from 50 to 900 mg/day. These same dosage levels are employed for the treatment and prevention of vascular disease, as well as for specifically lowering levels of Lp(a) and elevating HDL-cholesterol, and for treating and preventing diabetes.

Further embodiments of this invention are pharmaceutical compositions comprising a compound of Formula II together with pharmaceutically acceptable excipients, carriers, or diluents. The compounds are formulated for convenient oral, parenteral, or rectal administration, with oral delivery being preferred. Typical pharmaceutical carriers and excipients utilized in oral formulations include lactose, sucrose, starches, such as cornstarch and potato starch; cellulose derivatives such as methyl and ethyl cellulose; gelatins; talc; oils such as vegetable oils, sesame oil, cottonseed oil; and glycols such as polyethylene glycol. Oral preparations typically are in the form of tablets, capsules, emulsions, solutions, and the like. Controlled release formulations, for example, using a polymeric matrix or an osmotic pump, or the like, are also utilized. Typical formulations contain from about 5% to 95% by weight of a compound of Formula II administered with the excipient or carrier. Flavoring agents such as cherry flavor or orange flavor are incorporated.

For parenteral administration, the compounds are optionally formulated with diluents such as isotonic saline, 5% aqueous glucose, and the like, for convenient intramuscular and intravenous delivery. The compounds optionally also are formulated with waxes and gels in the form of suppositories. Topical compositions, for example creams and skin patches, can also be prepared according to conventional methods.

In order to more fully demonstrate the advantages of the present invention, the following detailed examples are set forth. It is to be understood that the following examples are for illustration only and should not be construed as a limitation on the scope of the present invention. All citations to references, including patents, are incorporated herein by reference.

EXAMPLE 1

Preparation of 6-(5-carboxy-5-methyl-hexyloxy)-2,2-dimethylhexanoic acid monocalcium salt hydrate, crystalline Form 1

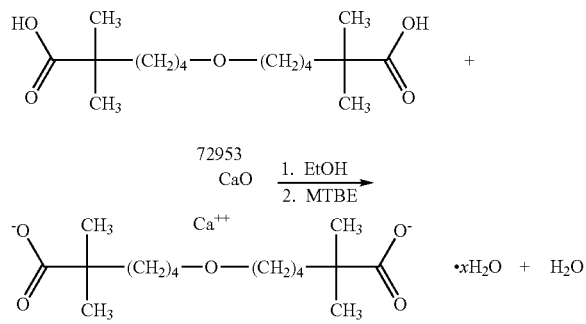

Pilot Scale Example to Prepare CI-1027 Hydrate Crystal Form 1 via Ethanol Solvate.
Charge to 750 L glass-lined still:
6-(5-carboxy-5-methyl-hexyloxy)-2,2-dimethylhexanoic acid; (72953)—54.4 Kg, 179.9 mol;
Calcium Oxide 98%—10.2 Kg, 178.2 mol;
Ethyl Alcohol, pure anhydrous—392 Kg, 497 L.
Start agitation (stirring) and heat mixture to reflux (76–80° C.). Reflux reaction mixture for 96 hours. Cool to 45° C. Charge to reaction mixture:
Methyl tert-Butyl Ether (MTBE)—128 Kg, 163 L.
Cool reaction mixture to 20° C. to 25° C. and stir approximately 1 hour. Filter solid product by centrifugation to provide CI-1027 ethanol solvate (Formula II, $R_1$ is $CH_3CH_2$—). Wash solid product with:
MTBE—307 Kg, 391 L.
Discharge product cake from centrifuge. Charge solvent wet product cake (CI-1027 ethanol solvate) to 400 L agitated pan dryer. Seal dryer and apply vacuum on the system. Set jacket temperature for 85° C. Start agitation after approximately 1 hour at 85° C. and full vacuum. Stir product at 85° C. and full vacuum for 12 to 16 hours. Set jacket temperature to 100° C. Close valve to vacuum source.

Charge by way of vacuum blank through injection nozzle:
Water, HPLC grade—6.4 Kg.
Water will vaporize and humidify the system. Stir the sealed, humidified system for 4 hours. Re-apply vacuum and dry product for 18 to 24 hours. Cool system to 25° C. Purge off vacuum with nitrogen. Discharge dry product from the dryer to give CI-1027 hydrate Crystal Form 1 as a white solid. Mill dry product through a Fitzmill with a #1A screen (The Fitzmill Company, Elmhurst, Ill.). Overall yield: 55.2 Kg (uncorrected for 4.04% water), 90.9%.

Analytical Results:
$C_{16}H_{28}O_5Ca.H_2O$—Infrared (KBr): 1107.3, 1416.2, 1477.9, 1552 $cm^{-1}$
Identification ($^1$H NMR)—(CDCl$_3$): δ 7.2, 3.4, 1.5, 1.2.
Identification (HPLC retention time)—Waters Symmetry C18 column; 150×4.6 mm; 8.46 minutes
Assay (HPLC wt/wt %)—99.30%
Ethyl Alcohol Content (wt % VPC)—0.06%
Water Content determined by thermogravemetric analysis (TGA)—3.45%
Calcium Content (by inductively coupled plasma method [ICP], corrected for water)—12.91%
Sodium Content—0.08%
XRD—CI-1027 hydrate Crystalline Form 1, see FIG. 1.
$^{13}$C NMR (solid state) in ppm 189.6; 186.2; 71.4; 43.4; 30.1; 28.4; 25.2*; 23.1

The * indicates a resonance considered unique for this Crystal Form 1.

Pilot Scale Data

Upon further scale-up of the foregoing CI-1027 hydrate Crystal Form 1 process, difficulties were encountered in drying the final product. The monocalcium salt ethanol solvate was formed in refluxing ethyl alcohol as described above. The removal of the ethyl alcohol from the isolated CI-1027 hydrate Crystal Form 1 product proved very difficult at larger scale using typical maximum drying conditions (100° C., full vacuum) and vacuum tray dryers. Different types of agitated dryers were investigated. Although some small-scale lots were dried to acceptable levels of ethyl alcohol, the results were inconsistent and the conditions applied were not conducive to further scale-up. See Table A for drying examples. The various lots (all prepared substantially as described above) are identified as "CD-number".

A preferred process for forming the hydrate is to expose the CI-1027 solvate product to humidity. The added humidity greatly accelerates the removal rate of the ethyl alcohol and facilitates production of the hydrate. This method was initially applied to the vacuum tray dryers with some success. The further application to agitated pan dryers resulted in a process whereby the ethyl alcohol was easily removed in a short time period. This humidified drying process produced consistent crystalline product in short cycle times and therefore demonstrates feasibility for large-scale manufacturing use.

The initial drying method, without the use of humidity, produced a CI-1027 hydrate product with an amorphous physical form as determined by x-ray diffraction (for example, Lots CD-2969C-3111 in Table A). The humidification process comprises drying the alcohol solvate at an elevated temperature of about 50° C. to about 150° C. in the presence of about 80% to about 95% relative humidity. The ethanol solvate from above was dried in a humidified agitated pan dryer to produce a CI-1027 hydrate Crystal Form 1 product with a crystalline form as determined by x-ray diffraction. Subsequently, it was observed that the crystalline form exhibited significant advantages over the amorphous form. The CI-1027 hydrate Crystalline Form 1 (Lots CD-3103-3243 in Table A) has a higher bulk density than amorphous CI-1027 as shown in Table B. The bulk density of the amorphous form was observed to be decreasing with increasing production scale. The crystalline form, however, was consistently produced with high bulk density, and is also observably less electrostatic than the amorphous form, a characteristic that greatly improves the handling characteristics of the bulk product. It should be noted that solvent free amorphous CI-1027 product also can be converted directly to CI-1027 hydrate Crystalline Form 1 by exposure to humidification. Solvent content is not required for the conversion to the Crystalline Form 1 product.

In summary, the advantages of the humidification process and resultant crystalline product include the following:

1. The humidification process allows for the effective drying of the CI-1027 hydrate Crystal Form 1 at a large scale. It produces a consistent, substantially alcohol solvent free product in a much shorter time period.
2. The resultant crystalline, alcohol solvent free CI-1027 hydrate Crystal Form 1 product generally exhibits a higher bulk density than amorphous CI-1027. This bulk density has been reasonably consistent upon scale-up, whereas the amorphous bulk density was observed to drop upon scale-up.
3. The resultant crystalline, alcohol free CI-1027 hydrate Crystal Form 1 product is observably less electrostatic than the amorphous product. This greatly improves the handling characteristics of the bulk product in large-scale production operations, and in subsequent fill/finish operations for the pharmaceutical dosage form.

TABLE A

Drying Time Experiments/Results

| Lot ID | Drying Method | Time (hrs) | Solvent Content |
|---|---|---|---|
| CD-2969C | Vac. Tray Dryer | 48 | 1.12% EtOH |
| | @ 72° C. | 24 | 1.08% EtOH |
| | @ 80° C. | 72 | 0.92% EtOH; 2.84% $H_2O$ |
| CD-3032 | Vac. Tray Dryer | 24 | 7.0% EtOH |
| | @ 82° C. | 24 | 6.0% EtOH |
| Milled here | → @ 82° C. | 24 | 5.5% EtOH |
| | @ 95° C. | 24 | 4.4% EtOH |
| | @ 95° C. | 72 | 0.9% EtOH; 1.24% $H_2O$ |
| CD-3044 | Vac. Tray Dryer @ 60° C. | 24 | 5.2% EtOH |
| | @ 82° C. | 24 | 4.1% EtOH |
| | @ 101° C. | 24 | 4.1% EtOH |
| Nitrogen bleed started here | → @ 102° C. | 18 | 2.0% EtOH |
| | @ 101° C. | 72 | 0.2% EtOH |
| | @ 101° C. | 72 | 0.1% EtOH; 1.5% $H_2O$ |
| CD-3055 | Vac. Tray Dryer @ 60° C. | 24 | 7.7% EtOH |
| Milled; moved | → @ 82° C. | 24 | 5.5% EtOH |
| into a rotary | → @ 104° C. | 24 | 4.7% EtOH |

TABLE A-continued

Drying Time Experiments/Results

| Lot ID | Drying Method | Time (hrs) | Solvent Content |
|---|---|---|---|
| dryer here | @ 105° C. | 24 | 3.4% EtOH |
| | @ 104° C. | 24 | 2.9% EtOH |
| | @ 101° C. | 24 | 2.5% EtOH |
| | @ 104° C. | 24 | 2.0% EtOH |
| | @ 101° C. | 24 | 2.0% EtOH |
| Moved to trays | → @ 103° C. | 24 | 0.3% EtOH |
| | @ 103° C. | 24 | 0.1% EtOH; 1.92% $H_2O$ |
| CD-3082 | Vac. Tray Dryer @ 82° C. | 24 | 5.97% EtOH |
| Milled here | → @ 98° C. | 24 | 0.85% EtOH |
| Added 5 L | → @ 97° C. | 24 | 0.72% EtOH |
| water in a tray | @ 97° C. | 24 | 0.41% EtOH |
| here | remilled | | 0.11% EtOH; 1.59% $H_2O$ |
| CD-3089 | Agitated Pan Dryer | | |
| | @ 82° C. | 24 | 7.1% EtOH |
| | @ 98° C. | 24 | 5.5% EtOH |
| | @ 100° C. | 24 | 5.1% EtOH |
| Moved to tray | → @ 100° C. | 20 | 1.8% EtOH |
| dryer. Added | @ 101° C. | 18 | 0.22% EtOH |
| 5 L water | @ 100° C. | 24 | 0.01% EtOH; 3.02% $H_2O$ |
| CD-3102 | Vac. Tray Dryer @ 84° C. | 20 | 6.7% EtOH |
| | @ 95° C. | 24 | 3.9% EtOH |
| | @ 95° C. | 24 | 1.77% EtOH |
| | @ 95° C. | 24 | 0.6% EtOH |
| | @ 95° C. | 72 | ND EtOH; 2.12% $H_2O$ |
| CD-3111 | Vac. Tray Dryer @ 81° C. | 24 | 5.4% EtOH |
| 10 trays | @ 98° C. | 24 | 0.07% EtOH |
| without covers. | @ 97° C. | 24 | 0.05% EtOH |
| Trays placed at | milled | | ND EtOH; 1.94% $H_2O$ |
| top of oven | | | |
| CD-3103* | Agitated Pan Dryer | | |
| | @ 80° C. | 24 | 5.4% EtOH |
| 1 Kg water | → @ 80° C. | 24 | 0.07% EtOH |
| added here | @ 100° C. | 24 | 0.05% EtOH |
| | milled | | 0.06% EtOH; 3.7% $H_2O$ |
| CD-3130* | Agitated Pan Dryer | | |
| | @ 85° C. | 24 | 5.9% EtOH |
| 2 Kg water | → @ 80° C. | 24 | 0.04% EtOH |
| added here | @ 100° C. | 24 | 0.06% EtOH |
| | milled | | 0.08% EtOH; 4.15% $H_2O$ |
| CD-3135* | Agitated Pan Dryer | | |
| | @ 80° C. | 24 | 5.76% EtOH |
| 2 Kg water | → @ 99° C. | 22 | 0.02% EtOH |
| added here | @ 98° C. | 5.5 | 0.02% EtOH |
| | milled | | ND EtOH; 4.38% $H_2O$ |
| CD-3172* | Agitated Pan Dryer | | |
| | @ 80° C. | 20 | 7.0% EtOH |
| 4 Kg water | → @ 100–102° C. | 19 | 0.2% EtOH |
| added here | @ 100° C. | 24 | 0.2% EtOH |
| CD-3321A* | Agitated Pan Dryer | | |
| | @ 80–85° C. | 18 | 6.27% EtOH |
| 6.4 Kg water | → @ 96–97° C. | 27 | 0.23% EtOH |
| added here | @ 97–98° C. | 19 | 0.06% EtOH |
| CD-3243* | Agitated Pan Dryer | | |
| | @ 85–87° C. | 19 | 7.22% EtOH |
| 6.4 Kg water | → @ 98–99° C. | 16 | 0.09% EtOH |
| added here | @ 99° C. | 18 | 0.06% EtOH |

The product is amorphous by XRD unless designated with * symbol.
The scale of product from CD-3172 was 35.1 Kg; from CD-3221A was 53.9 Kg; from CD-3243 was 49.3 Kg.
*Crystalline product by XRD analysis.
The extra drying time in these examples is because of the 24-hour turn around time for the ethyl alcohol analysis.

TABLE B

Bulk Density Results

| Lot ID | Bulk Density Loose (g/mL) | Bulk Density Tapped (g/mL) | XRD |
|---|---|---|---|
| CD-2969C | 0.336 | 0.439 | Amorphous |
| CD-3032 | 0.239 | 0.306 | Amorphous |
| CD-3044 | 0.249 | 0.279 | Amorphous |
| CD-3055 | 0.280 | 0.315 | Amorphous |
| CD-3082 | 0.234 | 0.337 | Amorphous |
| CD-3089 | 0.292 | 0.337 | Amorphous |
| CD-3102 | 0.215 | 0.270 | Amorphous |
| CD-3111 | 0.218 | 0.264 | Amorphous |
| CD-3103 | 0.343 | 0.484 | Crystalline |
| CD-3130 | 0.311 | 0.496 | Crystalline |
| CD-3135 | 0.242 | 0.379 | Crystalline |
| CD-3172 | 0.281 | 0.438 | Crystalline |
| CD-3221A | 0.372 | 0.521 | Crystalline |
| CD-3243 | 0.235 | 0.300 | Crystalline |

EXAMPLE 2

Preparation of Crystalline 6-(5-carboxy-5-methyl-hexyloxy)-2,2-dimethylhexanoic acid monocalcium salt, ethyl alcohol solvate

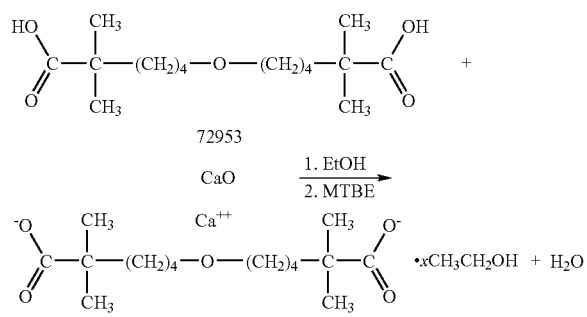

Standard Laboratory Method

Charge to 500 mL, 3-neck, round bottom flask with heating mantle, reflux condenser, and overhead stirring:

6-(5-carboxy-5-methyl-hexyloxy)-2,2-dimethylhexanoic acid; (72953)—25.0 g, 0.08267 mol;

Calcium Oxide 98%—1.0 equivalent, 0.08267 mol, 4.73 g (corrected for purity);

Ethyl Alcohol—187.5 g, 237 mL.

Start moderate agitation (stirring) and heat mixture to reflux (76–80° C.). Reflux reaction mixture for 4 to 24 hours. Cool to about 45° C.

Charge to reaction mixture:
MTBE—60.0 g, 79.2 mL.

Cool reaction mixture to 20° C. to 25° C. and stir approximately 1 hour. Filter off solid product.

Wash solid product with:
MTBE—40.0 g, 50 mL.

Dry product at 60° C. to 100° C. and full vacuum to constant weight. Discharge from dryer. White solid. Overall yield: 21 g (20 g dry basis) (corrected for water and ethyl alcohol content), 80% of title compound.

Figure 2:
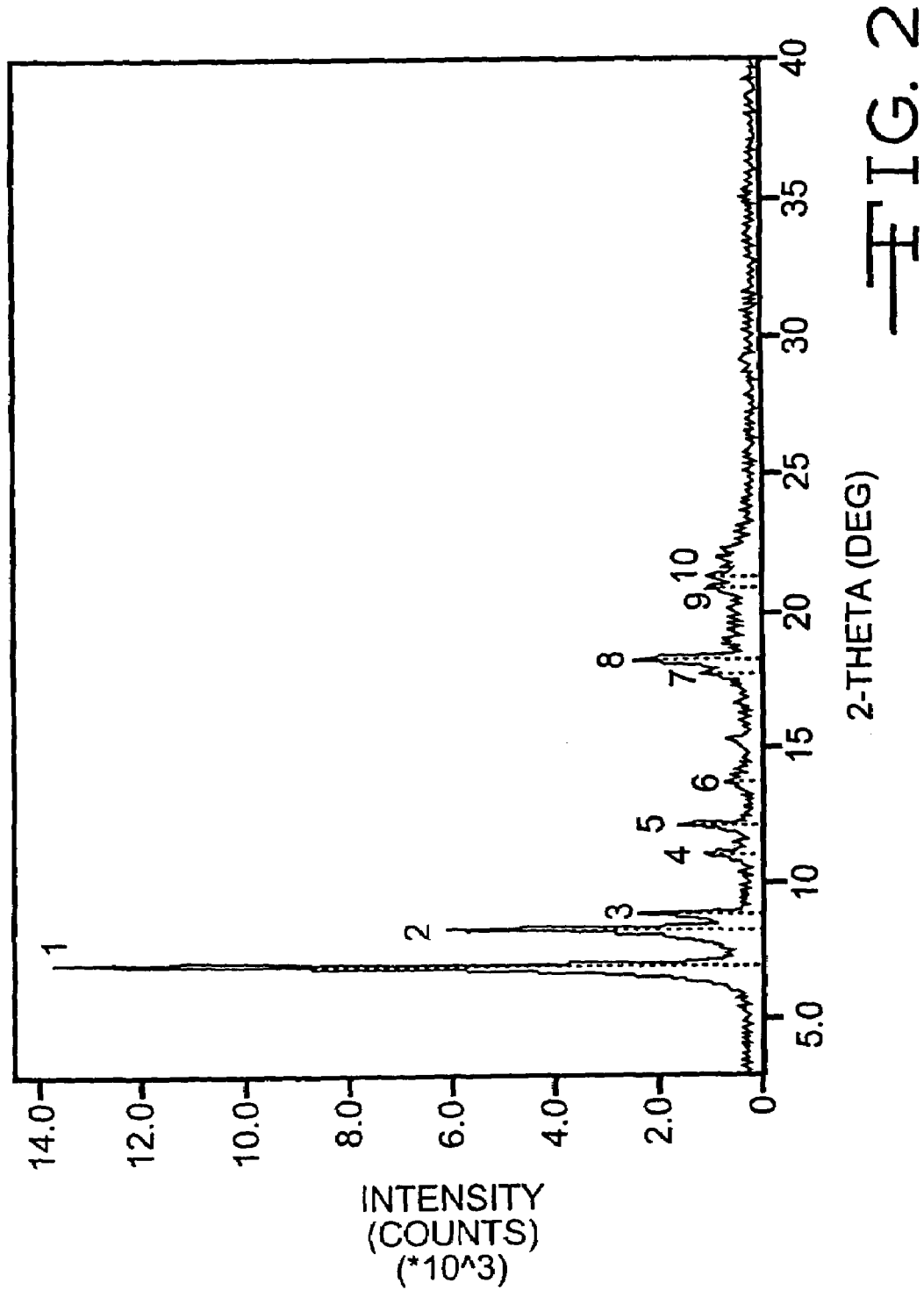
FIG. 2 is a two-dimensional drawing of the x-ray powder diffractogram of the ethyl alcohol solvate of the dicarboxylate ether monocalcium salt CI-1027.

Analytical Results:
Identification (IR)—KBr: 1107.3, 1552 cm$^{-1}$
Identification ($^1$H NMR)—(CDCl$_3$): δ 7.2.
HPLC (Area % CI-1027)—99.738%
Ethyl Alcohol Content (wt % VPC)—1.95%
Water Content (KF titration)—1.73% (avg. of 3)
Calcium Content (ICP, corrected for water)—10.82%
XRD—Crystalline solvate, see FIG. 2.
$^{13}$C NMR (solid state) in ppm 189.9; 186.7; 71.6; 58.5*; 43.2; 29.9; 23.5

The * indicates a resonance considered unique for this crystal form.

EXAMPLE 3

Preparation of 6-(5-carboxy-5-methyl-hexyloxy)-2,2-dimethylhexanoic acid monocalcium salt hydrate, Crystalline Form 1

Standard Laboratory Method (This is a summary of repeated reactions following the same procedure.)

Charge to jacketed 500 mL, 3-neck, round bottom flask with overhead stirrer, vacuum gauge, water injection nozzle, and external temperature bath: 50 g of 6-(5-carboxy-5-methyl-hexyloxy)-2,2-dimethylhexanoic acid monocalcium salt, ethyl alcohol solvate prepared as described in Example 2.

Seal reactor and start agitation (60–100 rpm). Pull full house vacuum on the system. Set jacket temperature for 60° C. Stir product at 60° C. and full vacuum for 18 hours. Close valve to vacuum source. Charge by way of vacuum blank through injection nozzle: Water—20 g.

Water will vaporize and humidify the reaction system. Stir the sealed, humidified system for 4 hours. Reapply vacuum and dry product for 20.5 hours. Cool system to below 30° C. and purge off vacuum with nitrogen. Discharge dry product from the reactor. Product is a white chunky solid. Overall yield:

24.89 g of title product.

Figure 3:
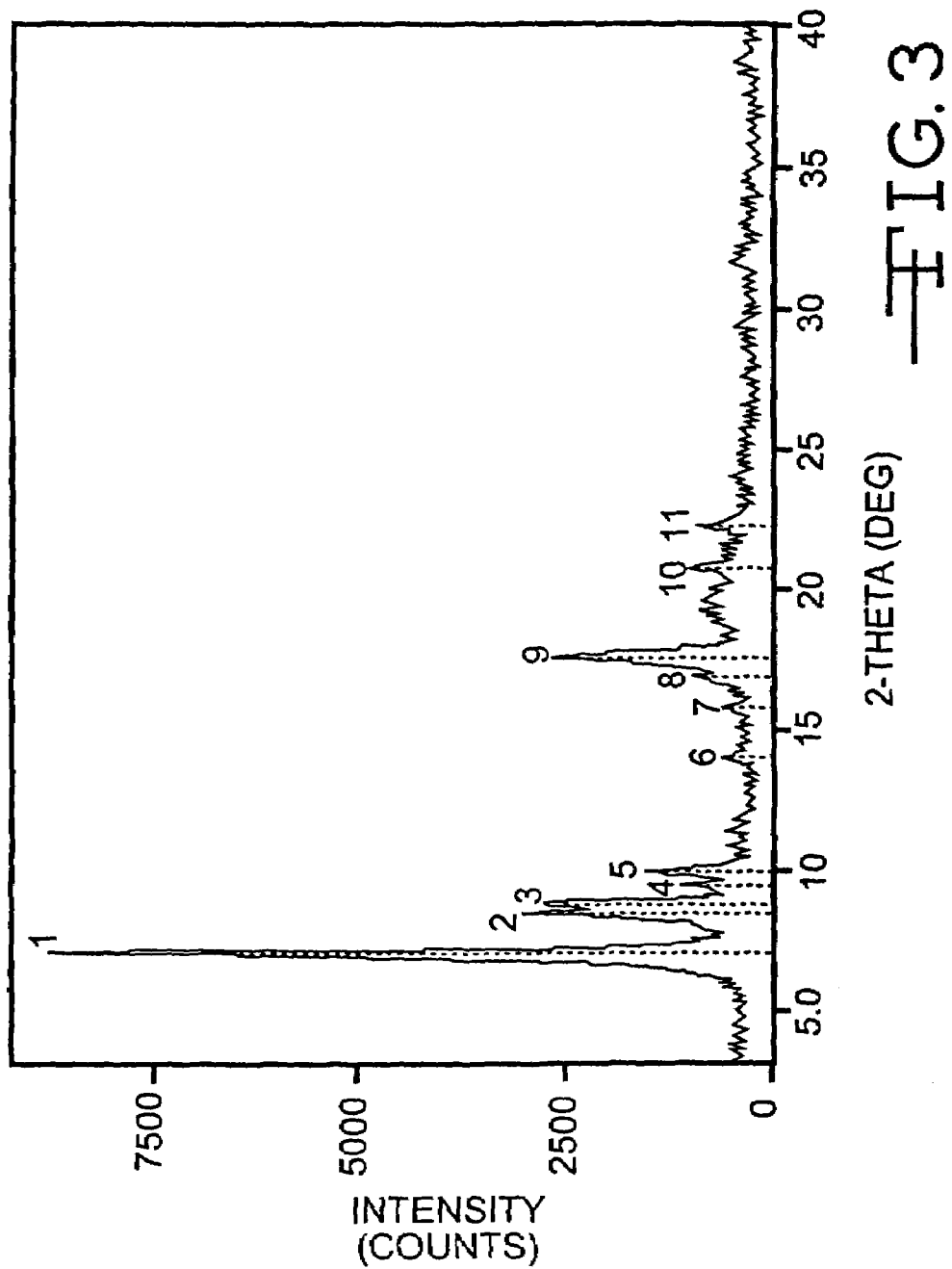
FIG. 3 is a two-dimensional drawing of the x-ray powder diffractogram of CI-1027 Crystal Form 1 (3.25% water) after humidification and drying of the ethyl alcohol solvate of the dicarboxylate ether monocalcium salt.

Analytical Results:
HPLC (Area % CI-1027)—99.725%
Ethyl Alcohol Content (wt % VPC)—0.0%
Water Content (KF titration)—3.25%
XRD analysis established the product to be CI-1027 Crystalline Form 1, see FIG. 3.

EXAMPLE 4

Preparation of Crystalline 6-(5-carboxy-5-methyl-hexyloxy)-2,2-dimethylhexanoic acid monocalcium salt, methyl alcohol solvate

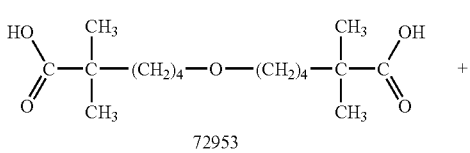

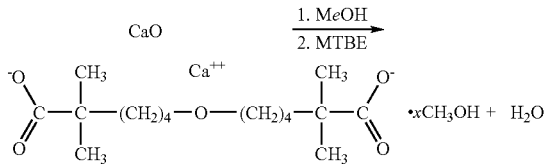

Methyl Alcohol Solvate

Standard Laboratory Method

Charge to 500 mL, 3-neck, round bottom flask with heating mantle, reflux condenser, and overhead stirring:

6-(5-carboxy-5-methyl-hexyloxy)-2,2-dimethylhexanoic acid; CI-1027 Step 1 (72953)—25.0 g, 0.08267 mol;

Calcium Oxide 98%—1.0 equivalent, 0.08267 mol, 4.73 g (corrected for purity).

Methyl Alcohol—187.5 g, 237 mol.

Start moderate agitation (50-60 rpm stirring) and heat mixture to reflux (64–66° C.). Reflux reaction mixture for 21 hours. Cool to 45° C. Charge to reaction mixture:

MTBE—60.0 g, 79.2 mL.

Cool reaction mixture to 20° C. to 25° C. and stir approximately 1 hour. Filter off solid product. Wash solid product with:

MTBE—40.0 g, 50 mL.

Product is white solid with gray chunks—50.87 g

Dry product at 60° C. with full vacuum for 3 hours to weight (21.75 g). Dry at 80° C. for 16 hours to weight of 16.34 g. Dry at 100° C. for 4.5 hours to weight of 10.97 g. Discharge from dryer. Product is a white crystalline solid.

Analytical Results:

HPLC (Area % CI-1027)—99.737%

Water Content (KF titration)—3.36% to 4.94% (range of 3 runs)

Figure 4:
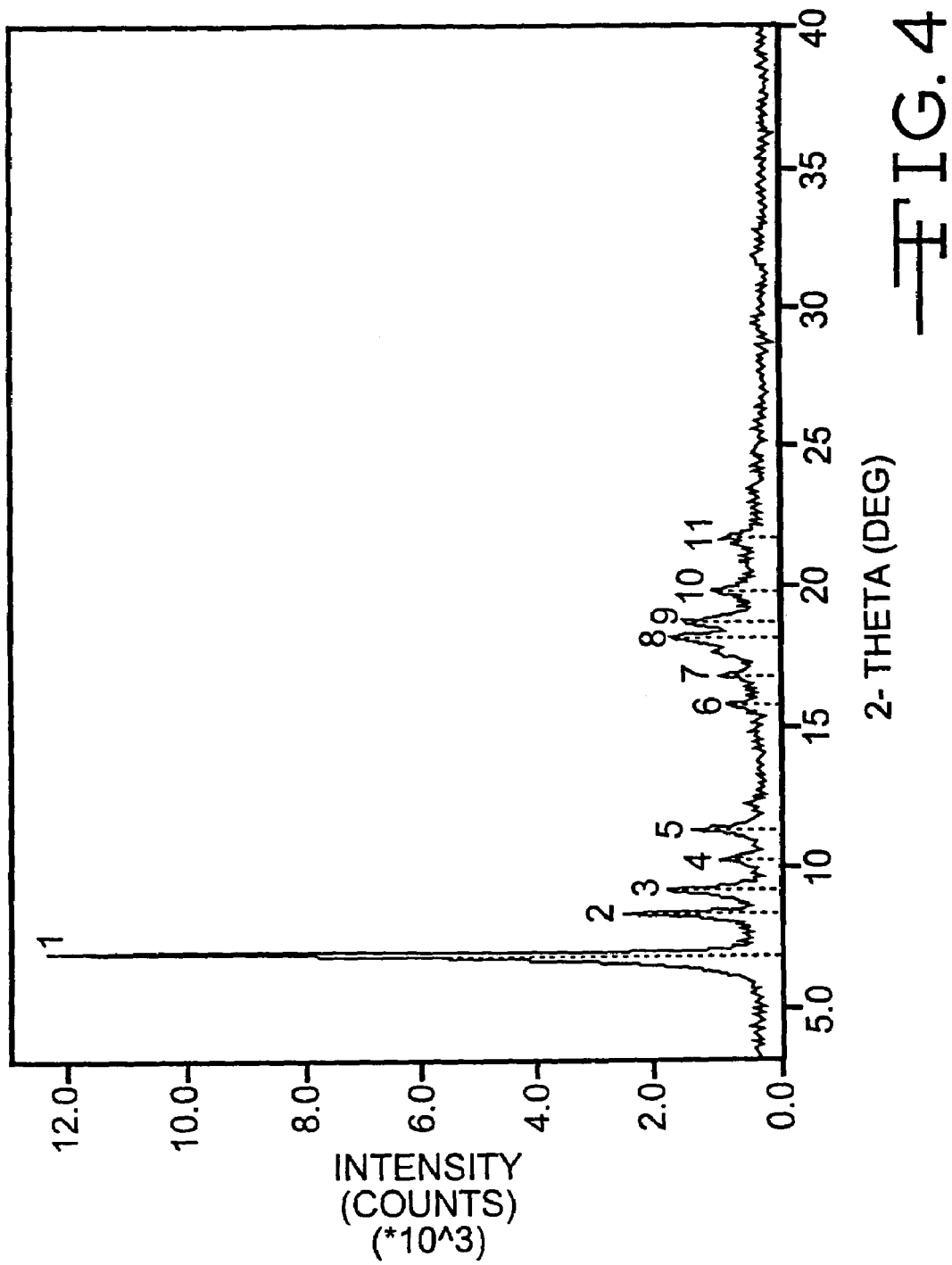
FIG. 4 is a two-dimensional drawing of the x-ray powder diffractogram of the methyl alcohol solvate of CI-1027.

Calcium Content (ICP, corrected for water)—11.00% to 11.22% (water range) XRD—CI-1027 methyl alcohol crystalline solvate, see FIG. 4.

$^{13}$C NMR (solid state) in ppm: 189.6; 186.2; 71.4; 43.2; 29.6; 23.5

EXAMPLE 5

Preparation of 6-(5-carboxy-5-methyl-hexyloxy)-2,2-dimethylhexanoic acid monocalcium salt, Crystalline Form 1 from methyl alcohol solvate Standard Laboratory Method Charge to jacketed 500 mL, 3-neck, round bottom flask with overhead stirrer, vacuum gauge, water injection nozzle, and external temperature bath:

6-(5-carboxy-5-methyl-hexyloxy)-2,2-dimethylhexanoic acid monocalcium salt; methyl alcohol solvate, prepared in Example 4.

Seal reactor and start agitation (60–100 rpm). Pull full house vacuum on the system. Set jacket temperature for 100° C. Close valve to vacuum source. Charge by way of vacuum blank through injection nozzle: Water—10 g.

Water will vaporize and humidify the system at 100° C. Stir the sealed, humidified system for 60 minutes. Reapply vacuum and dry product for 2 hours. Cool system to 25° C. Purge off vacuum with nitrogen. Discharge dry product from the reactor to provide crystalline white free flowing powder: 4.22 g.

Analytical Results:

HPLC (Area % CI-1027)—99.24%

Ethyl Alcohol Content (wt % VPC)—0.0%

Water Content (KF titration)—3.84%

Calcium Content (ICP, corrected for water)—11.52%

Figure 5:
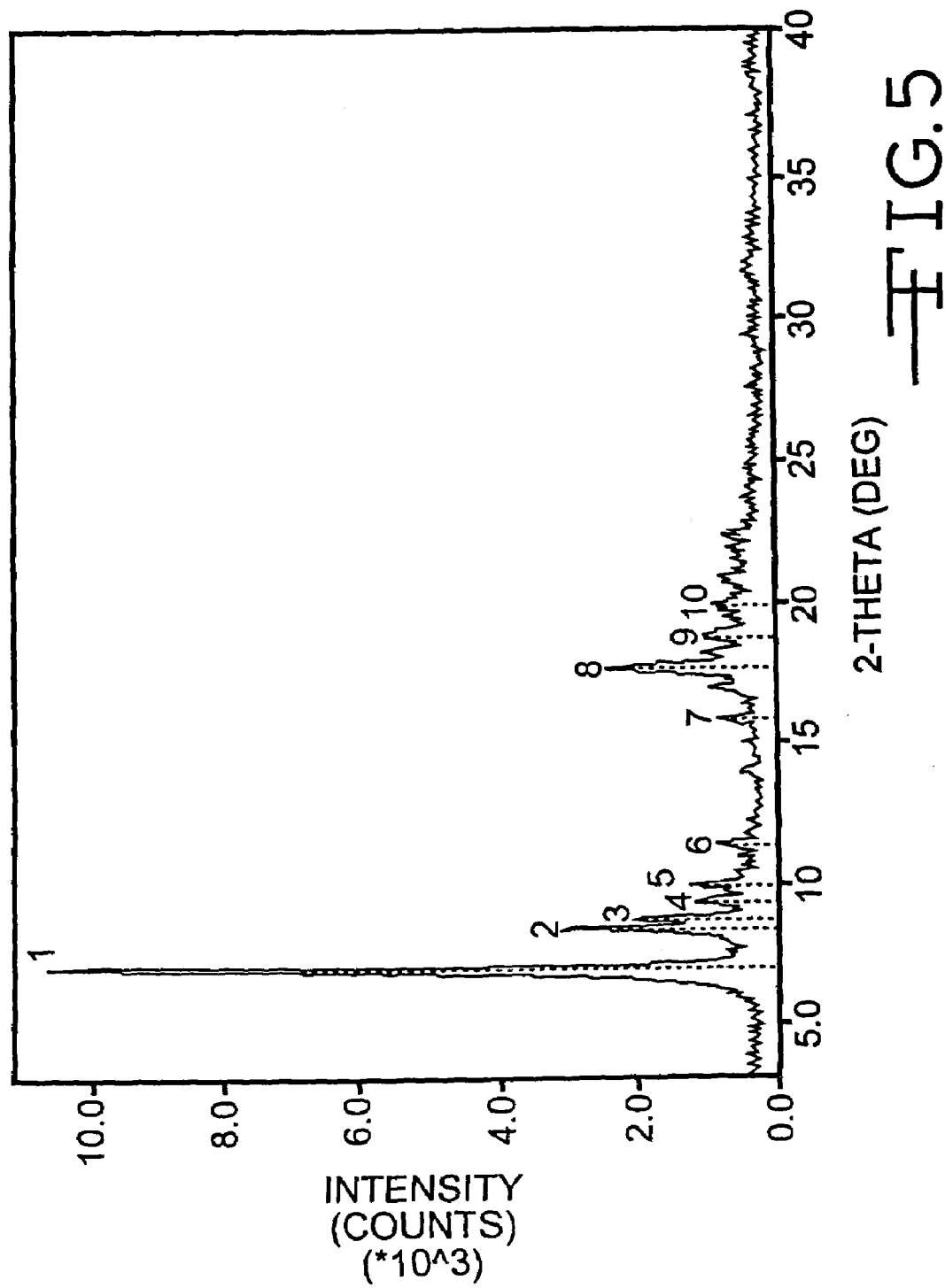
FIG. 5 is a two-dimensional drawing of the x-ray powder diffractogram of CI-1027 hydrate Crystal Form 1 after humidification and drying of the methyl alcohol solvate of the dicarboxylate ether monocalcium salt.

XRD—Crystalline Form I, see FIG. 5.

EXAMPLE 6

Preparation of Crystalline 6-(5-carboxy-5-methyl-hexyloxy)-2,2-dimethylhexanoic acid monocalcium salt, 1-propyl alcohol solvate

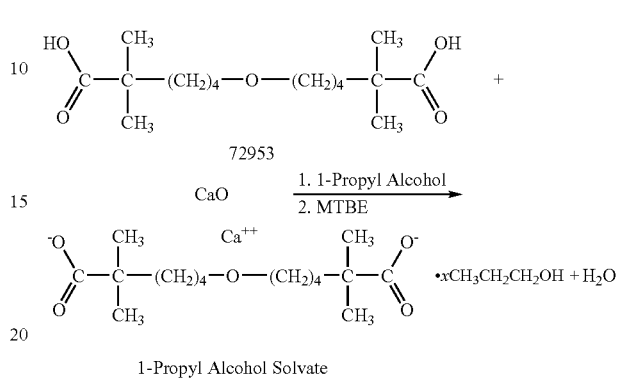

Standard Laboratory Method

Charge to 500 mL, 3-neck, round bottom flask with heating mantle, reflux condenser, and overhead stirring:

6-(5-carboxy-5-methyl-hexyloxy)-2,2-dimethylhexanoic acid; CI-1027 Step 1 (72953)—25.0 g, 0.08267 mol;

Calcium Oxide 98%—1.0 equivalent, 0.08267 mol, 4.73 g (corrected for purity); 1-Propyl Alcohol—187.5 g, 233 mL.

Start moderate agitation (50 rpm) and heat mixture to reflux (95–98° C.). Reflux reaction mixture for 12 hours. Cool to less than 50° C. Charge to reaction mixture:

MTBE—60.0 g, 79.2 mL.

Cool reaction mixture to 20° C. to 25° C. and stir approximately 1 hour. Filter off solid product. Wash solid product with:

MTBE—40.0 g, 50 mL.

Product is clay-like white solid—69.06 g.

Dry product at 60° C. and full vacuum for 16 hours (weight 29.52 g). Dry product at 80° C. for 3.5 hours to 23.53 g. Dry product at 100° C. for 2 hours to 18.03 g. Discharge from dryer to give white solid.

Analytical Results:

HPLC (Area % CI-1027)—99.064%

1-Propyl Alcohol Content (TGA)—5.99%

Water Content (KF titration)—1.72% (avg. of 2 runs)

Calcium Content (ICP, corrected for water)—10.73%

XRD—CI-1027 Crystalline 1-propyl alcohol solvate, see FIG. 6.

$^{13}$C NMR (solid state) in ppm 189.9; 186.0; 71.6; 43.2; 29.6; 23.8

EXAMPLE 7

Preparation of 6-(5-carboxy-5-methyl-hexyloxy)-2,2-dimethylhexanoic acid monocalcium salt, Crystalline Form 1 from 1-propyl alcohol solvate Standard Laboratory Method Charge to jacketed 500 mL, 3-neck, round bottom flask with overhead stirrer, vacuum gauge, water injection nozzle, and external temperature bath:

6-(5-carboxy-5-methyl-hexyloxy)-2,2-dimethylhexanoic acid monocalcium salt; 1-propyl alcohol solvate, prepared in Example 6.

Seal reactor and start agitation (60–100 rpm). Pull full vacuum (best available) on the system. Set jacket temperature for 100° C. Close valve to vacuum source. Charge by way of vacuum blank through injection nozzle: Water—10 g.

Water will vaporize and humidify the system. Stir the sealed, humidified system for 30 minutes. Reapply vacuum and dry product for 2 hours. Cool system to below 25° C. Purge off vacuum with nitrogen. Discharge product from the reactor to provide white course powder—10.33 g.

Figure 7:
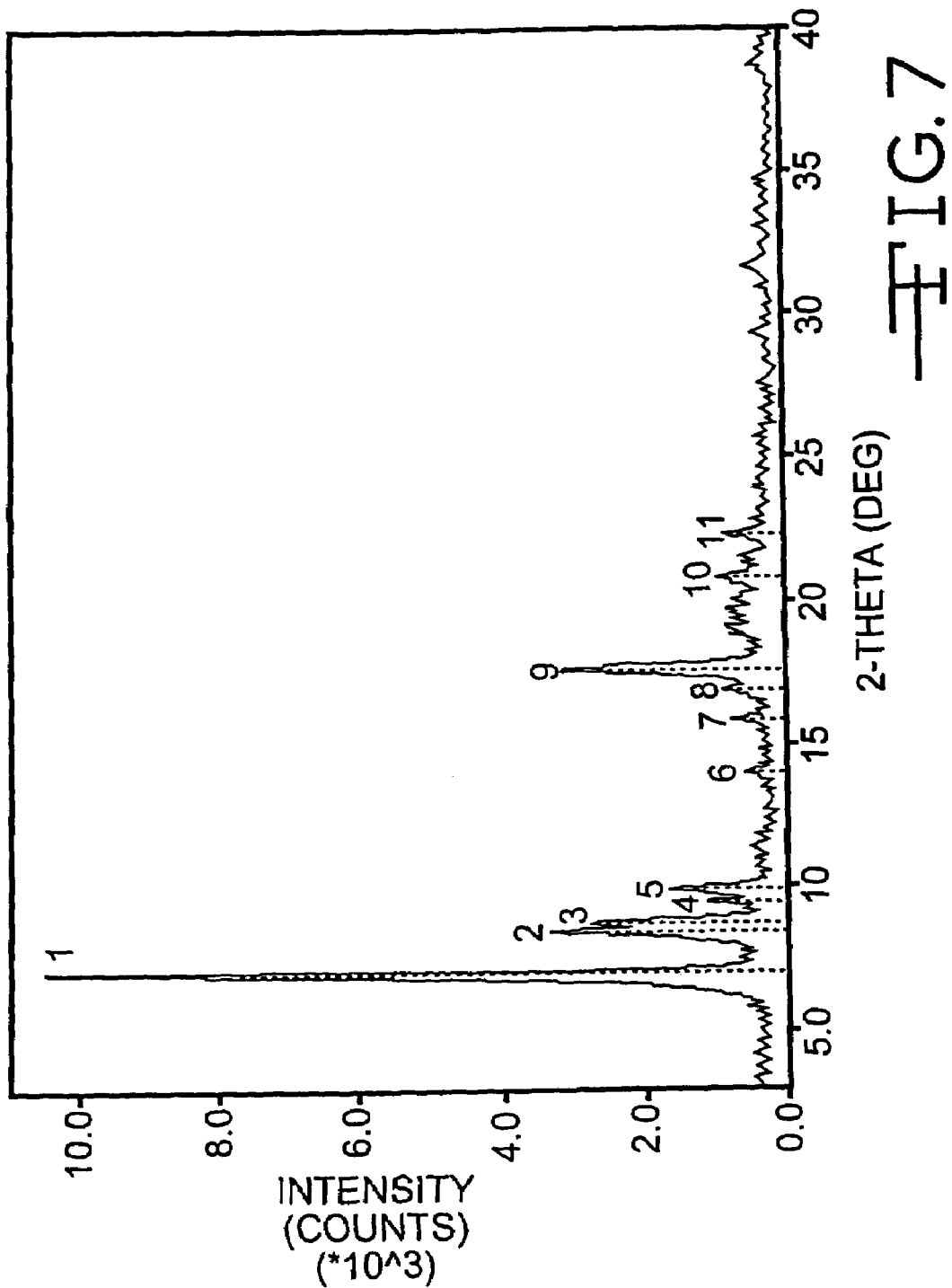
FIG. 7 is a two-dimensional drawing of the x-ray powder diffractogram of CI-1027 Crystal Form 1 (3.98% water) after humidification and drying of the 1-propyl alcohol solvate.

Analytical Results:
HPLC (Area % CI-1027)—99.519%
1-Propyl Alcohol Content (TGA)—0.0%
Water Content (KF titration)—3.98% (avg. of 2)
Calcium Content (ICP, corrected for water)—10.20%
XRD—CI-1027 Crystalline Form 1, see FIG. 7.

EXAMPLE 8

Preparation of Crystalline 6-(5-carboxy-5-methyl-hexyloxy)-2,2-dimethylhexanoic acid monocalcium salt, 2-propyl alcohol solvate

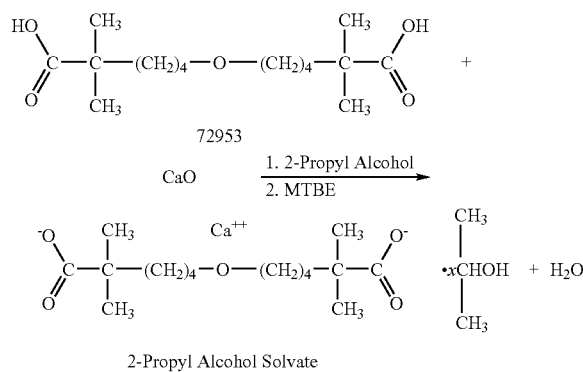

Standard Laboratory Method
Charge to 500 mL, 3-neck, round bottom flask with heating mantle, reflux condenser, and overhead stirring:
6-(5-carboxy-5-methyl-hexyloxy)-2,2-dimethylhexanoic acid; (72953)—25.0 g, 0.08267 mol
Calcium Oxide 98%—1.0 equivalent, 0.08267 mol, 4.73 g (corrected for purity) 2-Propyl Alcohol—187.5 g, 239 mL
Start moderate agitation (50 rpm) and heat mixture to reflux (80–83° C.). Reflux reaction mixture for 24 hours. Cool to 40° C. Charge to reaction mixture:
MTBE—60.0 g, 79.2 mL.
Cool reaction mixture to 20° C. to 25° C. and stir approximately 1 hour. Filter off solid product. Wash solid product with:
MTBE—40.0 g, 50 mL.
Product is white solid—50.90 g.
Dry product at 60° C. and full vacuum for 3 hours to weight of 28.59 g. Dry at 80° C. for 16 hours to 23.27 g. Dry at 100° C. for 4 hours to 17.51 g. Discharge from dryer to provide crystalline white solid.

Figure 8:
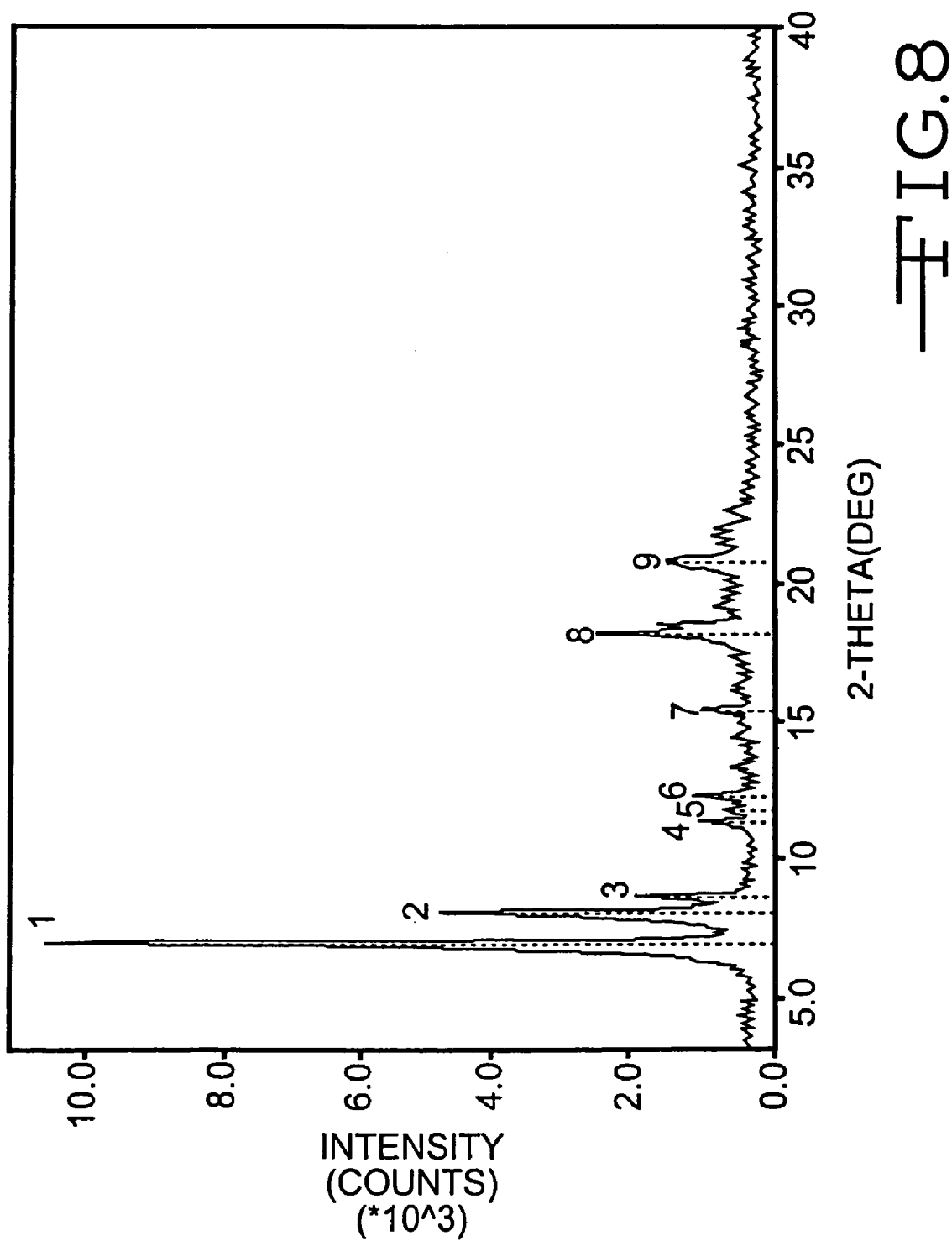
FIG. 8 is a two-dimensional drawing of the x-ray powder diffractogram of the 2-propyl alcohol solvate of CI-1027.

Analytical Results:
HPLC (Area % CI-1027)—99.315%
2-Propyl Alcohol Content (TGA)—6.12%
Water Content (KF titration)—1.96% (avg. of 3)
Calcium Content (ICP, corrected for water)—10.27%
XRD—CI-1027 2-propyl alcohol crystalline solvate, see FIG. 8.
$^{13}$C NMR (solid state) in ppm 189.4; 187.7; 70.9; 69.4; 66.5; 63.8*; 43.2; 35.0; 30.1; 23.8; 18.7*; 14.3*

The * indicates a resonance considered unique for this form.

EXAMPLE 9

Preparation of 6-(5-carboxy-5-methyl-hexyloxy)-2, 2-dimethylhexanoic acid monocalcium salt, Crystalline Form 1 from 2-propyl alcohol solvate Standard Laboratory Method
Charge to jacketed 500 mL 3-neck round bottom flask with overhead stirrer, vacuum gauge, water injection nozzle, and external temperature bath:
6-(5-carboxy-5-methyl-hexyloxy)-2,2-dimethylhexanoic acid monocalcium salt; 2-propyl alcohol solvate, prepared in Example 8.
Seal reactor and start agitation (60–100 rpm). Pull full vacuum on the system. Set jacket temperature for 100° C. Close valve to vacuum source. Charge by way of vacuum blank through injection nozzle: Water—10 g.
Water will vaporize and humidify the system. Stir the sealed, humidified system for 60 minutes. Reapply vacuum and dry product for 12 hours. Cool system to below 30° C. Purge off vacuum with nitrogen. Discharge product from the reactor to provide a free flowing powder—9.01 g.

Figure 9:
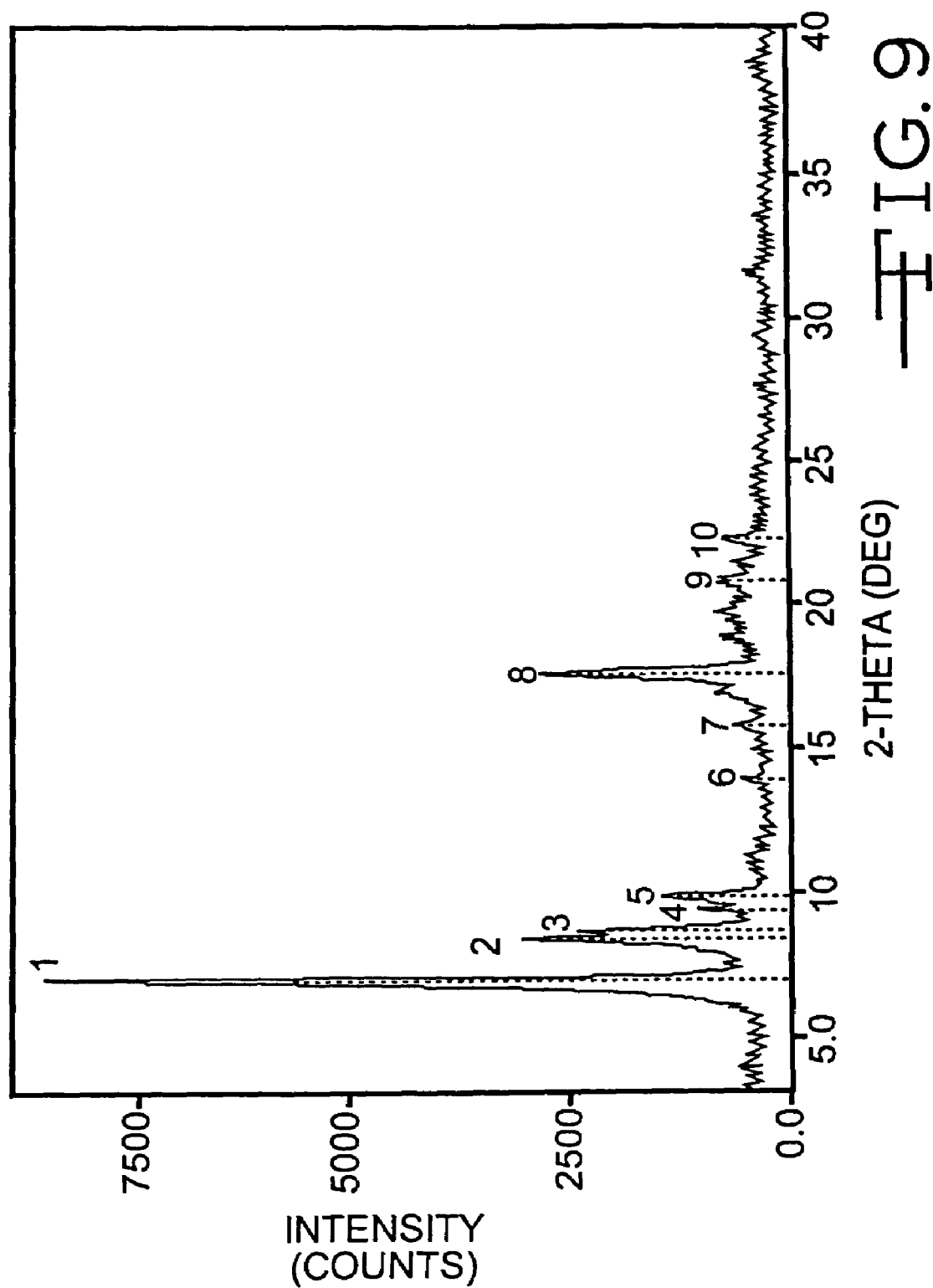
FIG. 9 is a two-dimensional drawing of the x-ray powder diffractogram of a compound of Formula II CI-1027 hydrate Crystal Form 1 after humidification and drying of the 2-propyl alcohol solvate of the dicarboxylate ether monocalcium salt.

Analytical Results:
HPLC (Area % CI-1027)—99.611%
2-Propyl Alcohol Content (TGA)—0.0%
Water Content (KF titration)—4.04% (avg. of 2)
Calcium Content (ICP, corrected for water)—10.93%
XRD—CI-1027 Crystalline Form 1, see FIG. 9.

EXAMPLE 10

Preparation of Crystalline 6-(5-carboxy-5-methyl-hexyloxy)-2,2-dimethylhexanoic acid monocalcium salt, 1-butyl alcohol solvate

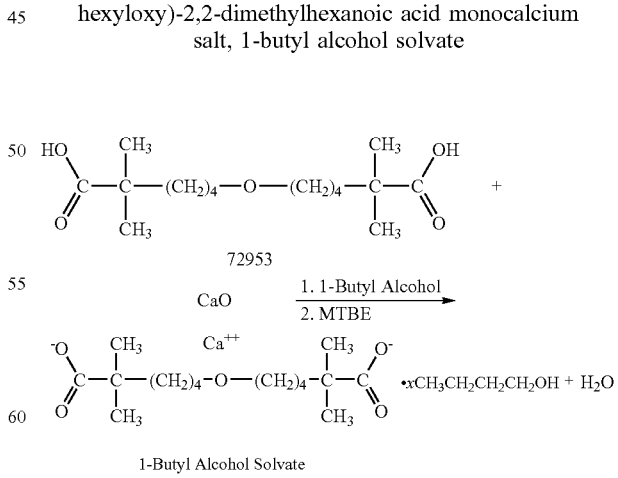

Standard Laboratory Method
Charge to 500 mL, 3-neck, round bottom flask with heating mantle, reflux condenser, and overhead stirring:

6-(5-carboxy-5-methyl-hexyloxy)-2,2-dimethylhexanoic acid; (72953)—25.0 g, 0.08267 mol;
Calcium Oxide 98%—1.0 equivalent, 0.08267 mol, 4.73 g (corrected for purity); 1-Butyl Alcohol—187.5 g, 231.5 mL.
Start moderate agitation and heat mixture to reflux (117–120° C.). Reflux reaction mixture for 12 hours. Cool to less than 50° C. Charge to reaction mixture:
MTBE—60.0 g, 79.2 mL.
Cool reaction mixture to 20° C. to 25° C. and stir approximately 1 hour. Filter off solid product. Wash solid product with: Methyl tert-Butyl Ether—40.0 g, 50 mL.
Product was white course solid—44.16 g.
Dry product at 60° C. at full vacuum for 16 hours to weight of 29.04 g. Dry at 80° C for 3.5 hours to 23.83 g. Dry at 100° C. for 2 hours to weight of 18.43 g. Discharge from dryer to give crystalline white solid.

Figure 10:
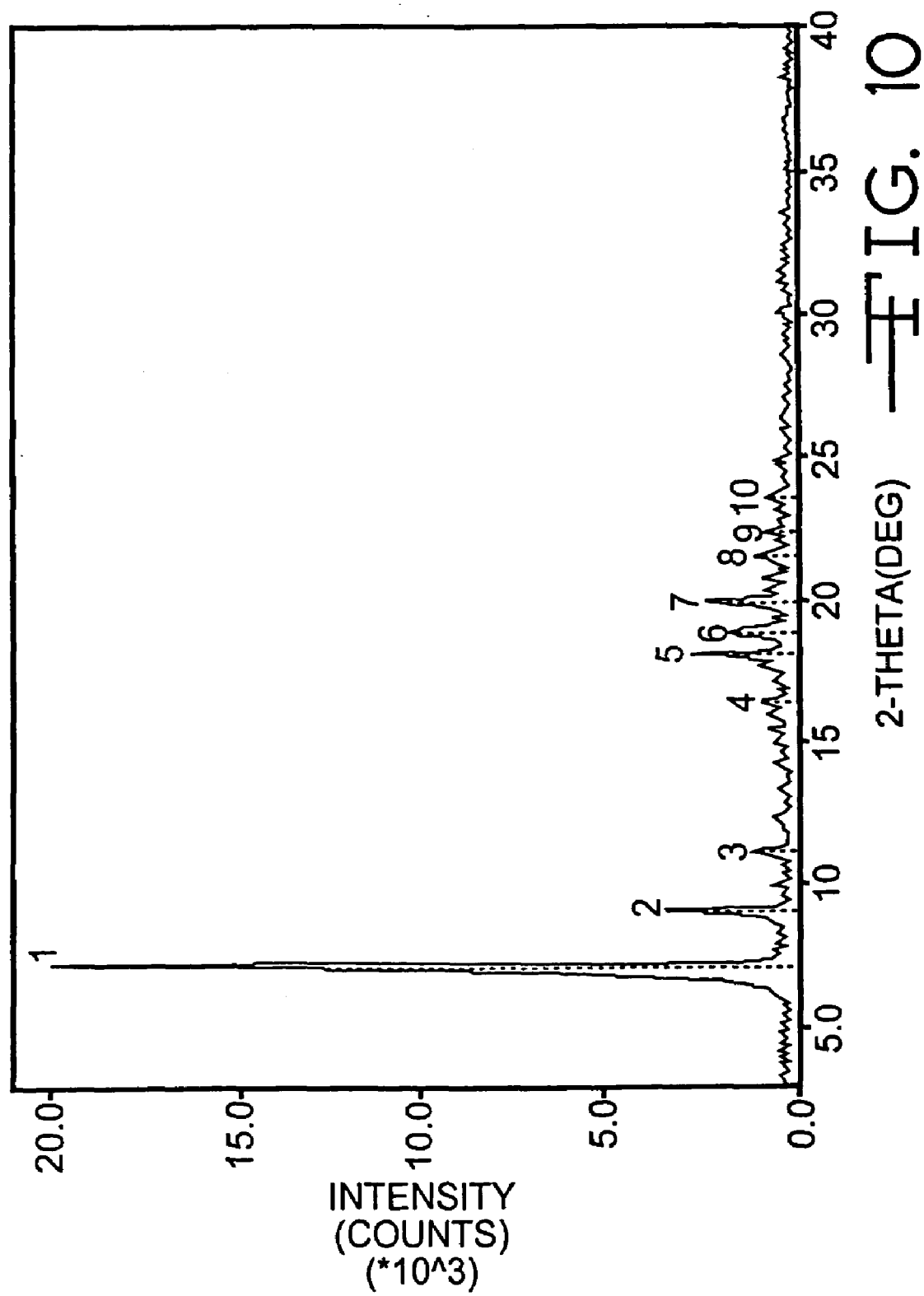
FIG. 10 is a two-dimensional drawing of the x-ray powder diffractogram of the 1-butyl alcohol solvate of CI-1027.

Analytical Results:
HPLC (Area % CI-1027)—99.560%
1-Butyl Alcohol Content (TGA)—9.02%
Water Content (KF titration)—1.93% (avg. of 2)
Calcium Content (ICP, corrected for water)—9.65%
XRD—CI-1027 Crystalline 1-butyl alcohol solvate, see FIG. 10.
$^{13}$C NMR (solid state) in ppm 189.9; 186.0; 71.6; 43.2; 29.9; 23.8

EXAMPLE 11

Preparation of 6-(5-carboxy-5-methyl-hexyloxy)-2,2-dimethylhexanoic acid monocalcium salt, Crystalline Form 1 from 1-butyl alcohol solvate Standard Laboratory Method
Charge to jacketed 500 mL, 3-neck, round bottom flask with overhead stirrer, vacuum gauge, water injection nozzle, and external temperature bath:
6-(5-carboxy-5-methyl-hexyloxy)-2,2-dimethylhexanoic acid monocalcium salt; 1-butyl alcohol solvate, prepared in Example 10.
Seal reactor and start agitation (60–100 rpm). Pull full vacuum (best available) on the system. Set jacket temperature for 100° C. Close valve to vacuum source. Charge by way of vacuum blank through injection nozzle:
Water—10 g.
Water will vaporize and humidify the system. Stir the sealed, humidified system for 30 minutes. Reapply vacuum and dry product for 2 hours. Cool system to 25° C. Purge off vacuum with nitrogen. Discharge dry product from the reactor to give course granular solid—10.35 g.

Figure 11:
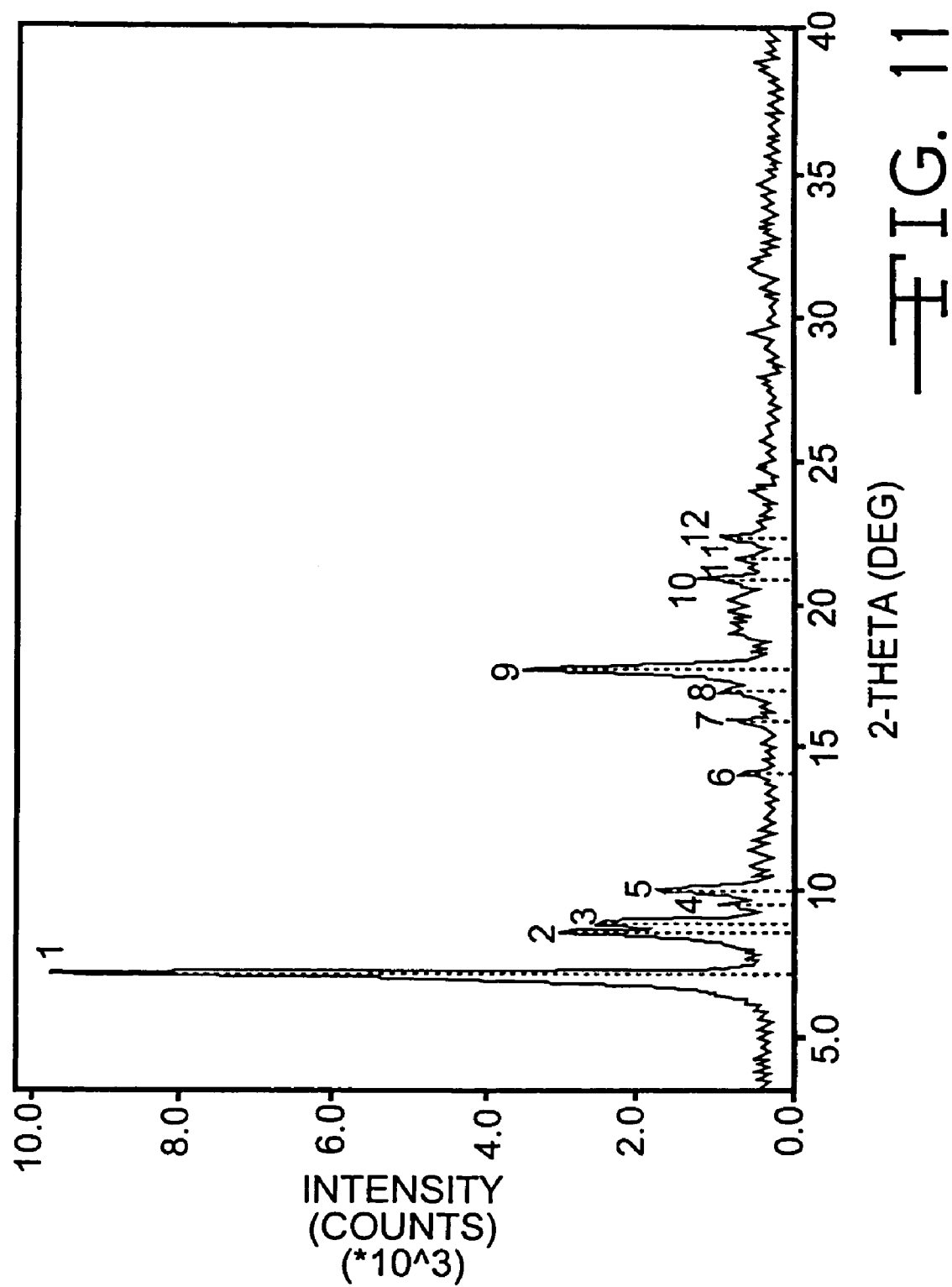
FIG. 11 is a two-dimensional drawing of the x-ray powder diffractogram CI-1027 hydrate Crystal Form 1 after humidification and drying of the 1-butyl alcohol solvate.
Figure 12:
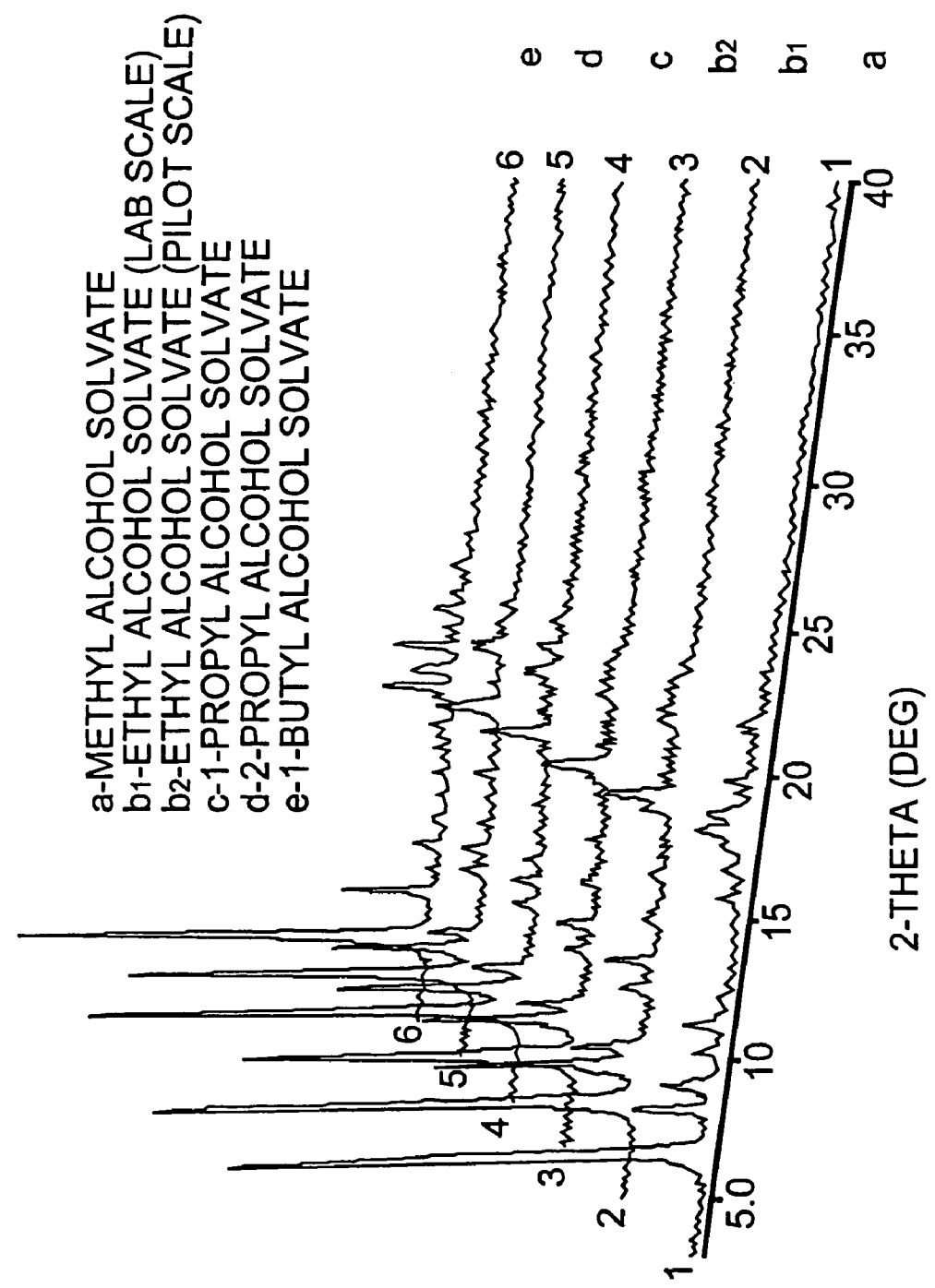
FIG. 12 is a three-dimensional comparison of x-ray powder diffractograms of the (a) methyl alcohol, (b) ethyl alcohol, (c) 1-propyl alcohol, (d) 2-propyl alcohol, and (e) 1-butyl alcohol solvates of the crystalline compounds of the present invention.
Figure 14:
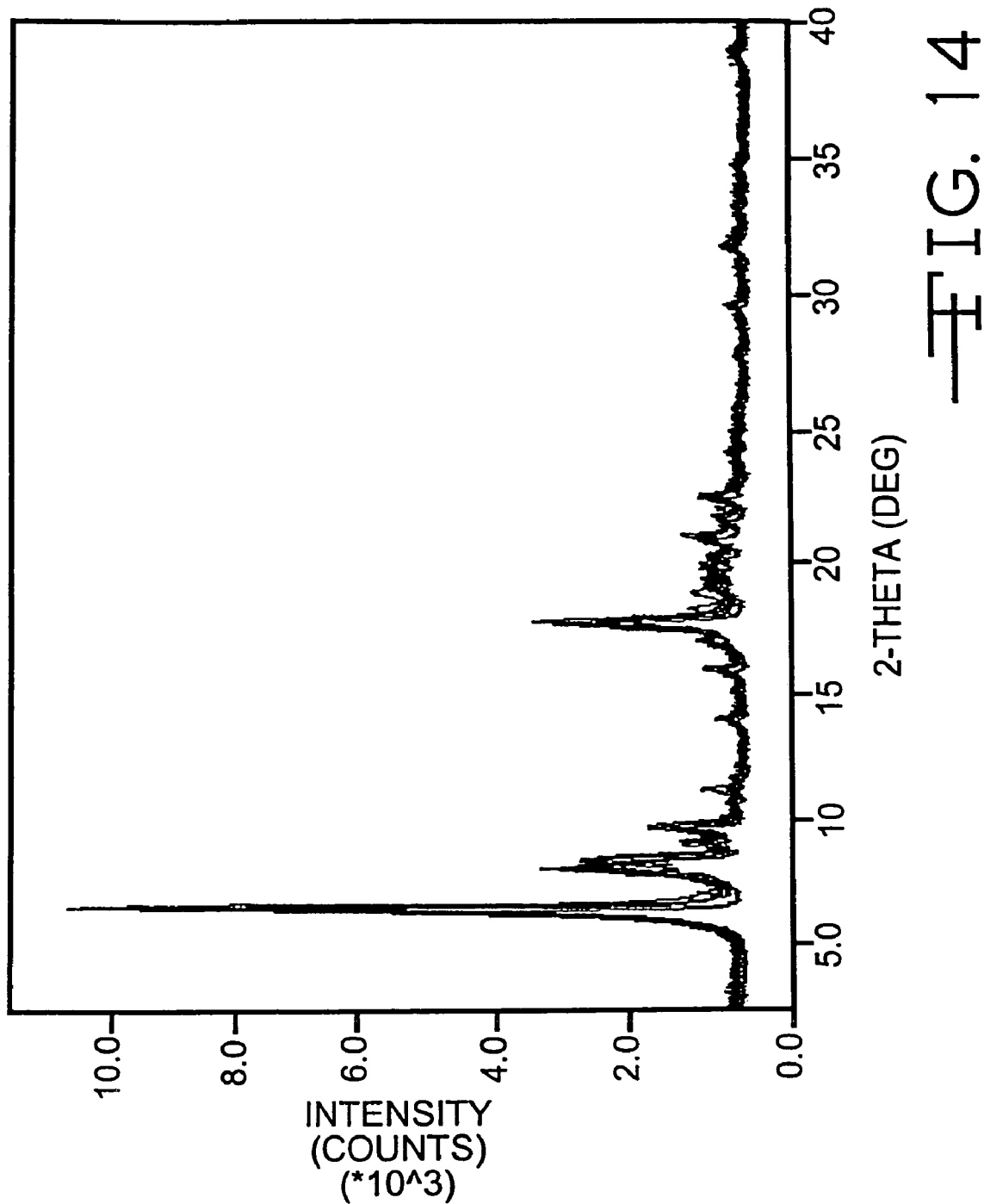
FIG. 14 is a two-dimensional overlay of the x-ray diffractograms of organic solvent free 6-(5-carboxy-5-methyl-hexyloxy)-2,2-dimethylhexanoic acid monocalcium salt produced from various alcohol solvates.

Analytical Results:
HPLC (Area % CI-1027)—99.374%
1-Butyl Alcohol Content (TGA)—0.0%
Water Content (KF titration)—3.96% (avg. of 3 runs)
Calcium Content (ICP, corrected for water)—10.70%
XRD—CI-1027 Crystalline Form 1, see FIG. 11.

EXAMPLE 12

Preparation of 6-(5-carboxy-5-methyl-hexyloxy)-2,2-dimethylhexanoic acid monocalcium salt. Crystalline Form 2 formed by water digestion Standard Laboratory Method
Charge to 200 mL round bottom flask:

6-(5-carboxy-5-methyl-hexyloxy)-2,2-dimethylhexanoic acid monocalcium salt; CI-1027 Crystalline Form 1 prepared using method of Pilot Plant Example 1—24.4 g
Water—100 g
The round bottom flask containing the slurry was attached to a rotary evaporator and a slow rotation initiated (120 rpm). The round bottom flask containing the slurry was then immersed in a water bath set for a temperature of 60° C. The aqueous suspension was stirred under atmospheric pressure for 7 days, and then the mixture was cooled to 20° C. to 25° C. The solids were collected by filtration and washed with 50 g of fresh water.
The solid product was dried at 90° C. under full vacuum to constant weight to give CI-1027 Crystal Form 2 hydrate as a white solid—21.3 g, 20.6 g dry basis (corrected for water), 84%.

Analytical Results:
HPLC (Area % CI-1027)—100.06%
Ethyl Alcohol Content (wt % VPC)—0.04%
Water Content (KF titration)—3.47%
Calcium Content (ICP, corrected for water)—10.78%
XRD—CI-1027 hydrate Crystalline Form 2, see FIG. 15.
$^{13}$C NMR (solid state) in ppm 190.9; 189.6; 186.2; 120.4; 72.7*; 44.7*; 44.2; 43.0; 42.3; 39.3; 37.9; 31.8; 30.9; 29.6; 27.7; 26.2*; 25.3; 24.0; 22.9; 21.5; and 20.2.

The * indicates a resonance considered unique for this form.

EXAMPLE 13

Preparation of Crystalline 6-(5-carboxy-5-methyl-hexlyoxy)-2,2-dimethylhexanoic acid monocalcium salt, Crystalline Form 2, formed by reaction with calcium hydroxide in water

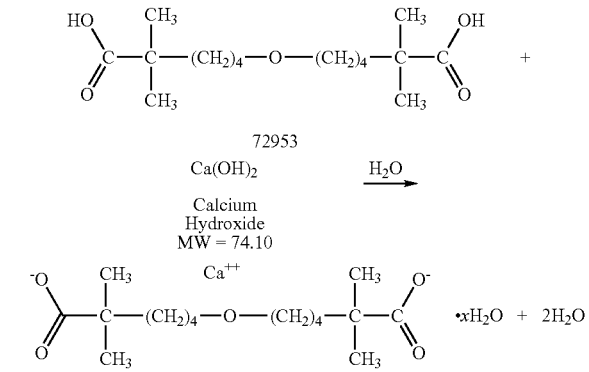

Standard Laboratory Method
Charge to 500 mL 3-neck, round bottom flask with heating mantle, reflux condenser, and overhead stirring:
6-(5-carboxy-5-methyl-hexyloxy)-2,2-dimethylhexanoic acid; (72953)—25.0 g, 0.08267 mol.
Calcium Hydroxide Powder—1.0 equivalent, 0.08267 mol, 6.13 g (uncorrected for purity).
Water—175 g, 175 mL.
Start agitation and heat mixture to 80° C. Stir reaction mixture at 80° C. for 12 hours. Cool reaction mixture to 0-5° C. Add 40 mL water to maintain stirrable mixture. Filter off solid product. White solid—49.34 g. Dry product at 95° C., full vacuum for 24 hours. Discharge from dryer. Chunky, white solid. Pulverize before bottling—14.62 g.

Analytical Results:
HPLC (Area % CI-1027)—99.60%
Water Content (KF titration)—4.93% (ave. of 2)
Calcium Content (ICP, corrected for water)—10.52%
XRD—CI-1027 Crystalline Form 2, see FIG. 15.

As noted in the forgoing examples, the calcium salts of Formula II, in various solvated forms, are solid and many are highly crystalline, thus making them especially useful for commercial manufacture and formulation. This unique solid nature and crystallinity of the calcium salts is surprising, given that other common salt forms have undesirable physical characteristics such as being hygroscopic and/or non-crystalline. Such hygroscopic and noncrystalline salt forms are unacceptable for large scale manufacturing and formulation operations. The following example further illustrates the advantages of the present calcium salts over the other salt forms.

EXAMPLE 14

Comparison of Monoalkali Earth Salts to other Salts

Following the general procedure of Example 1, 72953 was reacted with sodium hydroxide, potassium hydroxide, and acetylcholine in stoichiometric ratios of 1:1 per dialkanoic acid molecule, and 2:1 per dialkanoic acid molecule. The properties of the solids thus prepared, following complete drying, were compared to the calcium salt (CI-1027) from Example 1. The results are presented in Table 1.

TABLE 1

Salt Form and Hygroscopic Status

| Salt Prepared | Physical Form | Physical Properties of Solid |
|---|---|---|
| di-sodium | Solid | Very Hygroscopic |
| di-potassium | Solid | Very Hygroscopic |
| mono-choline | Oil | — |
| di-choline | Oil | — |
| mono-sodium | Solid | Hygroscopic |
| mono-potassium | Solid | Very Hygroscopic |
| mono-calcium | Solid and/or Crystalline | None to Slight Hygroscopic |

EXAMPLE 15

The effects of CI-1027 of Formula II, Crystalline Form 1, on Lp(a) and Other Lipoprotein Parameters in Two Models of Elevated Lp(a) were Determined by the Following in vivo Assays Cynomolgus macaque monkeys and Lp(a) transgenic mice are dosed with CI-1027 at 3, 10, 30, 100, or 300 mg/kg for 2 weeks by oral gavage. Lp(a) lowering is dose dependent (−9, −23, −64, −68, and −87% for the 3, 10, 30, 100, and 300 mg/kg/day doses, respectively). In these, studies total plasma and HDL cholesterol decreased. In the transgenic mouse study, female mice were allocated into five groups with equivalent Lp(a) levels, and dosed by oral gavage with either vehicle alone or vehicle plus CI-1027 (3, 10, 30, and 100 mg/kg/day). Blood is sampled weekly (2 weeks prior to treatment, 2 weeks on treatment). At the start of the study, plasma Lp(a) averaged 40 mg; (1 dL) across the groups. After 1 week, CI-1027 caused a dose dependent decrease in plasma Lp(a) (−15, −41, −54, and −61% for the 3, 10, 30, and 100 mg/kg/day dose levels, respectively) as compared to mice dosed with vehicle alone. There was also a dose-related decrease in total plasma, cholesterol, with a maximum decrease of 32% at the 100 mg/day dose. Lipoprotein profiles determined by HPLC demonstrated that the decrease in cholesterol is due primarily to significant decreases in LDL cholesterol. HDL cholesterol remained unchanged. The ratio of HDL cholesterol to VLDL+LDL cholesterol improved with treatment from a control value of 0.39 to 0.65. Plasma apoB was also decreased by up to 30%. Changes are similar following the second week of treatment.

EXAMPLE 16

The Effects of CI-1027 Crystal Form 1 on Insulin Sensitivity

CI-1027 is evaluated in a standard assay utilizing 3T3-L1 adipocytes, which are particularly responsive to insulin, ie, sugar uptake can be acutely activated 15- to 20-fold by insulin. The methodology utilized for the assay is described more fully by Frost, et al., *J Biol. Chem.*, 1985;260:2646–2652. Specifically, 3T3-L1 fibroblast cells were obtained from American Type Culture Collection (ATCC, Rockville, Md.). Cells were grown to confluence and differentiated into adipocytes. On Day 0, confluent cells were treated with 167 mm insulin, 0.25 µM dexamethasone, and 0.5 mM methyl isobutylmethylxanthine in 10% fetal bovine serum (FBS) containing Dulbecco's Modified Eagle's Medium (DMEM). Two days later, the media was changed to DMEM containing 167 nm insulin and 10% FBS. The media was then switched to 10% DMEM and changed every other day until harvest. CI-1027 solubilized in dimethyl sulfoxide, was included in the media on Day 0, and replenished with each media change. Differentiation was assessed by visualizing the accumulation of fat droplets in the cells. Glucose transport was measured by quantitating the incorporation of [$^{14}$C]deoxyglucose in differentiated cells on Day 9, according to the methodology described by Sandouk, et al., *Endocrinology*, 1993;133:352–359.

EXAMPLE 17

Pharmacokinetics and Metabolism of [$^{14}$C]CI-1027

CI-1027 is under clinical evaluation for the treatment of dyslipidemias and atherosclerosis by elevating high-density lipoprotein cholesterol (HDL-C) and lowering the atherogenic lipoprotein Lp(a). CI-1027 is rapidly absorbed in the rat, dog, and monkey. Oral bioavailability appeared to be high even though CI-1027 pharmacokinetics are nonlinear and the drug seemed to undergo enterohepatic recirculation. Apparent intravenous (IV) and per orals (PO) elimination half-life values are shorter in rat (5 to 7 hours) than in dog (17 to 31 hours) or in the monkey (9 to 15 hours). In vitro binding to plasma proteins is species and concentration dependent. Albumin appeared to be the primary binding protein. In vitro studies with rat, dog, and monkey hepatocytes using radiolabeled compound revealed two major $^{14}$C peaks, intact drug, and a glucuronide conjugate. Mean recovery (percent $^{14}$C dose) in intact and bile-fistula cannulated rats and monkeys following 10 mg/kg [$^{14}$C] is shown below in Table 2.

TABLE 2

Mean Recovery as Percent of 10 mg/kg and $^{14}$C dose

| Excreta | Intact Rat | Fistula Rat | Monkey | Fistula Monkey |
|---|---|---|---|---|
| Bile | | 87.5 | | 42.0 |
| Urine | 37.0 | 10.5 | 78.1 | 62.2 |

TABLE 2-continued

| | Mean Recovery as Percent of 10 mg/kg and $^{14}C$ dose | | | |
|---|---|---|---|---|
| Excreta | Intact Rat | Fistula Rat | Monkey | Fistula Monkey |
| Feces | 56.9 | 0.72 | 17.3 | 3.82 |
| Total | 93.9 | 98.7 | 95.4 | 108 |

Metabolite profiling is performed by HPLC with radiometric detection and metabolites are identified by LC/RAM/MS/MS. Essentially 100% of the plasma radioactivity was unchanged drug. Since an acyl-glucuronide is detected in bile and urine, LC/NMR analysis is performed to examine the potential acyl-migration products.

EXAMPLE 18

Capsule Formulation

| Ingredient | Amount |
|---|---|
| 6-(5-carboxy-5-methyl-hexyloxy)-2,2-dimethylhexanoic acid monocalcium salt hydrate Crystal Form 1 | 1000 g |
| Lactose | 960 g |
| Magnesium Stearate | 40 g |

The ingredients are blended to uniformity and filled into #4 hard gelatin capsules. Each capsule is filled with 200 mg of the blended mixture and contains 100 mg of active monocalcium dicarboxylate ether. The capsules are administered to an adult human at the rate of one to three each day to lower plasma Lp(a).

EXAMPLE 19

Tablet Formulation

| Ingredient | Amount |
|---|---|
| 6-(5-carboxy-5-methyl-hexyloxy)-2,2-dimethyl-1-hexanoic acid monocalcium salt hydrate Crystal Form 2 | 3000 g |
| Lactose | 750 g |
| Cornstarch | 300 g |
| Gelatin | 120 g |
| Water | 1000 cc |
| Magnesium stearate | 20 g |

The dialkyl ether salt, lactose, and 150 g of the cornstarch are blended with a solution of the gelatin in the water. The wet granulation is screened, dried, and re-screened. The dried granules are blended with the magnesium stearate and the remaining cornstarch, and the mixture is compressed into 698 mg tablets using 15/32 inch standard concave punches. Each tablet contains 500 mg of dialkyl ether salt.

EXAMPLE 20

Oral Liquid Formulation

| Ingredient | Amount |
|---|---|
| 6-(5-carboxy-5-methyl-hexyloxy)-2,2-dimethyl-1-hexanoic acid monocalcium salt hydrate Crystal Form 1 | 4.0 g |
| Polyoxyethylene sorbital monostearate | 0.1 cc |
| Sodium carboxymethyl cellulose | 0.3 g |
| Complex Magnesium Aluminum Silicate | 0.5 g |
| Sugar | 10 g |
| Glycerin | 2 cc |
| Sodium benzoate | 0.5 g |
| Sodium citrate | 0.2 g |
| Approved red dye | 1 mg |
| Cherry flavor | 0.02 cc |
| Distilled water qs | 100 cc |

The polyoxyethylene sorbital monostearate is a product such as polysorbate 60 or Tween 60. The complex magnesium-aluminum silicate is a gel-forming agent, such as Vcegum H.V. This substance is hydrated overnight in 10 cc of distilled water. A mixture is prepared from the polyoxyethylene sorbital monostearate, imitation cherry flavor, 30 cc of distilled water, and the alkaline earth dicarboxylate ether and passed through a homogenizer. With vigorous stirring, the sugar, glycerin sodium citrate, sodium benzoate, and sodium carboxymethylcellulose are added, followed by a hydrated complex of magnesium-aluminum silicate and a solution of the red dye in 2 cc of water. The resulting suspension is homogenized, adjusted to pH 5.0 with citric acid, and diluted to a final volume of 100 cc with distilled water. A 55-cc oral dosage unit of this suspension contains 100 mg of the dialkyl acid ether salt. If desired, the red dye and imitation cherry flavor can be omitted or replaced by other coloring and flavoring agents.

EXAMPLE 21

Coated Tablet Formulation

| Ingredients | Amount for 1000 tablets |
|---|---|
| Tablet Core | |
| 6-(5-carboxy-5-methyl-hexyloxy)-2,2-dimethyl-1-hexanoic acid monocalcium salt (CI-1027) | 168.92 |
| Lactose monohydrate NF | 36.00 |
| Hydroxypropyl cellulose | 18.80 |
| Croscarmellose sodium | 9.40 |
| Magnesium stearate (nonbovine) | 1.88 |
| Purified water, USP | qs |
| | 235.00 g |

The tablet core is prepared in a fluid bed granulator. An aqueous binder solution of hydroxypropyl cellulose in water is placed in a low shear mixer. The CI-1027 and lactose monohydrate are blended together in the fluid bed granulator. The binder solution is sprayed over the top of the mixture in the fluid bed granulator to produce granules. The granules are collected and passed through a Comil. The screened granules are mixed with the croscarmellose sodium in a blender to uniformity. Magnesium stearate is added to the blender and the mixture is stirred to uniformity. The mixture is pressed into 1000 tablets using a standard tablet press. The tablets are mixed in a coating pan with a solution of 7.00 g of Opandry White YS-1-7040 (Colorcon Inc., West Point, Pa.) and 0.05 g of simethicone emulsion USP (30% in water). The tablets are then coated with a film that facilitates storage and administration. Each tablet contains 168.92 mg of CI-1027, which is equivalent to 150 mg of 72953 (free acid).

The invention and the manner and process of making and using it are now described in such full, clear, concise, and exact terms as to enable any person skilled in the art to which it pertains, to make and use the same. It is to be understood that the foregoing describes preferred embodiments of the present invention, and that modifications may be made therein without departing from the spirit or scope of the present invention as set forth in the claims. To particularly point out and distinctly claim the subject matter regarded as invention, the following claims conclude this specification.

What is claimed is:

1. A compound that is 6-(5-carboxy-5-methyl-hexyloxy)-2,2-dimethylhexanoic acid monocalcium salt of formula II:

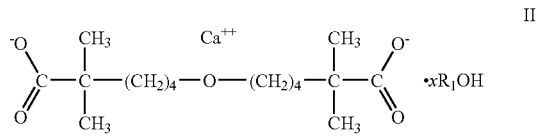

wherein $R_1$ is $C_1$–$C_4$ alkyl and x is a number from 1 to 10.

2. A crystalline compound selected from the group consisting of:

6-(5 -carboxy-5 -methyl-hexyloxy)-2,2-dimethylhexanoic acid monocalcium salt methanol solvate;

6-(5-carboxy-5 -methyl-hexyloxy)-2,2-dimethylhexanoic acid monocalcium salt ethanol solvate;

6-(5 -carboxy-5 -methyl-hexyloxy)-2,2-dimethylhexanoic acid monocalcium salt 1-propyl alcohol solvate;

6-(5-carboxy-5 -methyl-hexyloxy)-2,2-dimethylhexanoic acid monocalcium salt 2-propyl alcohol solvate; and 6-(5-carboxy-5-methyl-hexyloxy)-2,2-dimethylhexanoic acid monocalcium salt 1-butyl alcohol solvate.

3. The crystalline compound of claim 2 wherein said compound comprises 6-(5-carboxy-5-methyl-hexyloxy)-2,2-dimethylhexanoic acid monocalcium salt ethanol solvate.

4. The crystalline compound of claim 2 wherein said compound comprises 6-(5-carboxy-5-methyl-hexyloxy)-2,2-dimethylhexanoic acid monocalcium salt methanol solvate.

5. The crystalline compound of claim 2 wherein said compound comprises 6-(5-carboxy-5-methyl-hexyloxy)-2,2-dimethylhexanoic acid monocalcium salt 1 -propyl alcohol solvate.

6. The crystalline compound of claim 2 wherein said compound comprises 6-(5-carboxy-5-methyl-hexyloxy)-2,2-dimethylhexanoic acid monocalcium salt 2-propyl alcohol solvate.

7. The crystalline compound of claim 2 wherein said compound comprises 6-(5-carboxy-5-methyl-hexyloxy)-2,2-dimethylhexanoic acid monocalcium salt 1 -butyl alcohol solvate.

8. A pharmaceutical composition comprising a compound of claim 2 together with one or more pharmaceutically acceptable diluents, carriers or excipients.

9. A method of treating a vascular disease in a patient in need thereof, said method comprising administering to the patient a therapeutically effective amount of a compound of claim 2.

* * * * *